US008889751B2

(12) United States Patent
Liu et al.

(10) Patent No.: US 8,889,751 B2
(45) Date of Patent: Nov. 18, 2014

(54) POROUS MATERIALS, METHODS OF MAKING AND USES

(75) Inventors: Futian Liu, Sunnyvale, CA (US);
Nicholas J. Manesis, Summerland, CA (US); Alexei Goraltchouk, Santa Barbara, CA (US); Dimitrios Stroumpoulis, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 175 days.

(21) Appl. No.: 13/247,835

(22) Filed: Sep. 28, 2011

(65) Prior Publication Data

US 2012/0077012 A1 Mar. 29, 2012

Related U.S. Application Data

(60) Provisional application No. 61/387,074, filed on Sep. 28, 2010.

(51) Int. Cl.
*C08J 9/26* (2006.01)
*B29C 67/20* (2006.01)

(52) U.S. Cl.
CPC ........... *B29C 67/202* (2013.01); *C08J 2383/04* (2013.01); *C08J 9/26* (2013.01); *C08J 2201/0462* (2013.01)
USPC ................................ 521/61; 521/63; 521/154

(58) Field of Classification Search
CPC ... C08J 9/26; C08J 2201/0462; C08J 2383/04
USPC .............................................. 521/61, 63, 154
See application file for complete search history.

(56) References Cited

U.S. PATENT DOCUMENTS

| | | |
|---|---|---|
| 2,805,208 A | 9/1957 | Roche |
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,600,718 A | 8/1971 | Boone |
| 3,665,520 A | 5/1972 | Perras |
| 3,700,380 A | 10/1972 | Kitrilakis |
| 3,852,832 A | 12/1974 | McGhan |
| 3,934,274 A | 1/1976 | Hartley, Jr. |
| 4,034,751 A | 7/1977 | Hung |
| 4,157,085 A | 6/1979 | Austad |
| 4,231,979 A | 11/1980 | White |
| 4,237,237 A | 12/1980 | Jarre et al. |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,584,324 A | 4/1986 | Baumann et al. |
| 4,592,755 A | 6/1986 | Penton |
| 4,608,396 A | 8/1986 | Baumann et al. |
| 4,610,690 A | 9/1986 | Tiffamy |
| 4,636,213 A | 1/1987 | Pakiam |
| 4,643,733 A | 2/1987 | Becker |
| 4,647,618 A | 3/1987 | Baumann et al. |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl |
| 4,740,208 A | 4/1988 | Cavon |
| 4,772,285 A | 9/1988 | Ksander |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl et al. |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |

(Continued)

FOREIGN PATENT DOCUMENTS

| | | |
|---|---|---|
| EP | 0230672 | 8/1987 |
| EP | 0315814 | 5/1989 |

(Continued)

OTHER PUBLICATIONS

Brauker et al., "Neovascularization of synthetic membranes directed by membrane microarchitecture", Journal of Biomedical Materials Research, 1995, pp. 1517-1524, vol. 29, John Wiley & Sons, Inc.
Brohim et al., "Early Tissue Reaction to Textured Breast Implant Surfaces", Anals of Plastic Surgery, 28(4): 354-362.
Sharkawy et al. "Engineering the tissue which encapsulates subcutaneous implants", II. Plasma—tissue exchange properties, 1998, pp. 586-597, John Wiley & Sons, Inc.
Alvarez, Sonia et al., "Synthesis of Macro/Mesoporous Silica and Carbon Monoliths by Using a Commercial Polyurethane Foam as Sacrificial Template", Materials Letters, 61, 2378-2381 (2007).
Barr, S. et al., "Current Implant Surface Technology: An Examination of Their Nanostructure and Their Influence on Fibroblast Alignment and Biocompatibility", Elastic, 2009, 9, 198-217.
Barnsley, Philip et al., "Textured Surface Breast Implants in the Prevention of Capsular Contracture Among Breast Augmentation Patients: A Meta-Analysis of Randomized Controlled Trials", Plastic and Reconstructive Surgery, 2006, 117(7), 2182-2190.

(Continued)

*Primary Examiner* — Irina S Zemel
(74) *Attorney, Agent, or Firm* — Linda Allyson Fox

(57) ABSTRACT

The present specification discloses porous materials, methods of forming such porous materials, materials and devices comprising such porous materials, and methods of making such materials and devices.

4 Claims, 2 Drawing Sheets

(56) References Cited

U.S. PATENT DOCUMENTS

| | | | |
|---|---|---|---|
| 4,944,749 A | 7/1990 | Becker |
| 4,944,750 A | 7/1990 | Cox, Jr. |
| 4,950,292 A | 8/1990 | Audretsch |
| 4,955,907 A | 9/1990 | Ledergerber |
| 4,955,909 A | 9/1990 | Ersek |
| 4,960,425 A | 10/1990 | Yan |
| 4,965,430 A | 10/1990 | Curtis |
| 4,969,899 A | 11/1990 | Cox, Jr. |
| 5,002,572 A | 3/1991 | Picha |
| 5,007,929 A | 4/1991 | Quaid |
| 5,007,940 A | 4/1991 | Berg |
| 5,011,494 A | 4/1991 | von Recum et al. |
| 5,022,942 A | 6/1991 | Yan |
| 5,026,394 A | 6/1991 | Baker |
| 5,034,422 A | 7/1991 | Triolo |
| 5,035,249 A | 7/1991 | Sasaki |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,128,088 A | 7/1992 | Shimomura et al. |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iverson |
| 5,534,023 A | 7/1996 | Henley |
| 5,545,217 A | 8/1996 | Offray |
| 5,545,220 A | 8/1996 | Andrews |
| 5,549,671 A | 8/1996 | Waybright |
| 5,571,179 A | 11/1996 | Manders |
| RE35,391 E | 12/1996 | Brauman |
| 5,589,176 A | 12/1996 | Seare |
| 5,605,693 A | 2/1997 | Seare |
| 5,607,473 A | 3/1997 | Weber-Unger |
| 5,624,674 A | 4/1997 | Seare, Jr. |
| 5,630,843 A | 5/1997 | Rosenberg |
| 5,630,844 A | 5/1997 | Dogan |
| 5,653,755 A | 8/1997 | Ledergerber |
| 5,658,330 A | 8/1997 | Carlisle |
| 5,674,285 A | 10/1997 | Quaid |
| 5,681,572 A | 10/1997 | Seare, Jr. |
| 5,779,734 A | 7/1998 | Ledergerber |
| 5,776,159 A | 8/1998 | Picha |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,895,423 A | 4/1999 | Becker |
| 5,935,164 A | 8/1999 | Iversen |
| 5,961,552 A | 10/1999 | Iversen |
| 5,964,803 A | 10/1999 | Iversen |
| 5,965,076 A | 10/1999 | Banks |
| 5,984,943 A | 11/1999 | Young |
| 5,993,716 A * | 11/1999 | Draenert ............... 264/221 |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. |
| 6,214,926 B1 | 4/2001 | Winn |
| 6,315,796 B1 | 11/2001 | Eaton |
| 6,340,648 B1 | 1/2002 | Imura et al. |
| 6,387,133 B1 | 5/2002 | Perouse |
| 6,432,138 B1 | 8/2002 | Offray |
| 6,464,726 B1 | 10/2002 | Heljenek |
| 6,520,989 B1 | 2/2003 | Eaton |
| 6,531,523 B1 | 3/2003 | Davankov |
| 6,544,287 B1 | 4/2003 | Johnson |
| 6,602,452 B2 | 8/2003 | Schuessler |
| 6,605,116 B2 | 8/2003 | Falcon |
| 6,638,308 B2 | 10/2003 | Corbitt, Jr. |
| 6,673,285 B2 | 1/2004 | Ma |
| 6,692,527 B1 | 2/2004 | Bellin |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt, Jr. |
| 6,900,055 B1 | 5/2005 | Fuller |
| 6,913,626 B2 | 7/2005 | McGhan |
| 6,916,339 B1 | 7/2005 | Missana |
| 6,921,418 B2 | 7/2005 | Ledergerber |
| 6,932,840 B1 | 8/2005 | Bretz |
| 7,081,135 B2 | 7/2006 | Smith et al. |
| 7,081,136 B1 | 7/2006 | Becker |
| 7,105,116 B2 | 9/2006 | Bellin |
| 7,169,180 B2 | 1/2007 | Brennan |
| 7,192,450 B2 | 3/2007 | Brauker |
| 7,244,270 B2 | 7/2007 | Lesh |
| 7,323,208 B2 | 1/2008 | Ma |
| 7,476,249 B2 | 1/2009 | Frank |
| 7,520,896 B2 | 4/2009 | Benslimane |
| 7,547,393 B2 | 6/2009 | Ramaswamy |
| 7,625,405 B2 | 12/2009 | Purkait |
| 7,632,228 B2 | 12/2009 | Brauker |
| 7,632,291 B2 | 12/2009 | Stephens |
| 7,641,688 B2 | 1/2010 | Lesh |
| 7,645,475 B2 | 1/2010 | Prewett |
| 8,202,317 B2 | 6/2012 | Becker |
| 8,313,527 B2 | 11/2012 | Powell et al. |
| 8,506,627 B2 | 8/2013 | Van Epps et al. |
| 8,546,458 B2 | 10/2013 | Thompson et al. |
| 2002/0038147 A1 | 3/2002 | Miller |
| 2002/0193885 A1 | 12/2002 | Legeay |
| 2003/0036803 A1 | 2/2003 | McGhan |
| 2003/0093151 A1 | 5/2003 | Zhang |
| 2003/0105469 A1 | 6/2003 | Karmon |
| 2003/0205846 A1 | 11/2003 | Bellin |
| 2003/0208269 A1 | 11/2003 | Eaton |
| 2004/0010225 A1 | 1/2004 | Schuessler |
| 2004/0115241 A1 | 6/2004 | Calhoun |
| 2004/0127985 A1 | 7/2004 | Bellin |
| 2004/0143327 A1 | 7/2004 | Ku |
| 2004/0148024 A1 | 7/2004 | Williams |
| 2004/0153151 A1 | 8/2004 | Gonzales |
| 2004/0176493 A1 | 9/2004 | Ferguson |
| 2004/0213986 A1 | 10/2004 | Kim |
| 2005/0055093 A1 | 3/2005 | Brennan |
| 2005/0070124 A1 | 3/2005 | Miller |
| 2005/0112169 A1 | 5/2005 | Brauker |

(56) References Cited

U.S. PATENT DOCUMENTS

| | | |
|---|---|---|
| 2005/0122169 A1 | 6/2005 | Watanabe |
| 2005/0196452 A1 | 9/2005 | Boyan et al. |
| 2005/0216094 A1 | 9/2005 | Prewett |
| 2005/0251083 A1 | 11/2005 | Carr-Brendel et al. |
| 2006/0002810 A1 | 1/2006 | Grohowski |
| 2006/0036266 A1 | 2/2006 | Sulamandize et al. |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2007/0093911 A1 | 4/2007 | Fricke |
| 2007/0104693 A1 | 5/2007 | Quijano |
| 2007/0104695 A1 | 5/2007 | Quijano |
| 2007/0116735 A1 | 5/2007 | Calhoun |
| 2007/0135916 A1 | 6/2007 | Maxwell |
| 2007/0154525 A1 | 7/2007 | Calhoun |
| 2007/0190108 A1 | 8/2007 | Datta et al. |
| 2007/0198085 A1 | 8/2007 | Benslimane |
| 2008/0009830 A1 | 1/2008 | Fujimoto |
| 2008/0071371 A1 | 3/2008 | Elshout |
| 2008/0075752 A1 | 3/2008 | Ratner |
| 2008/0154366 A1 | 6/2008 | Frank |
| 2008/0241212 A1 | 10/2008 | Moses |
| 2008/0268019 A1 | 10/2008 | Badylak |
| 2008/0312739 A1 | 12/2008 | Agerup |
| 2009/0045166 A1 | 2/2009 | Li |
| 2009/0082864 A1 | 3/2009 | Chen |
| 2009/0087641 A1 | 4/2009 | Favis |
| 2009/0093878 A1 | 4/2009 | Glicksman |
| 2009/0118829 A1 | 5/2009 | Powell |
| 2009/0125107 A1 | 5/2009 | Maxwell |
| 2009/0169716 A1 | 7/2009 | Linhardt |
| 2009/0198331 A1 | 8/2009 | Kesten et al. |
| 2009/0198332 A1 | 8/2009 | Becker |
| 2009/0198333 A1 | 8/2009 | Becker |
| 2010/0042211 A1 | 2/2010 | Van Epps et al. |
| 2010/0075056 A1* | 3/2010 | Axisa et al. ............ 427/373 |
| 2010/0292790 A1 | 11/2010 | Stroumpoulis et al. |
| 2011/0054605 A1 | 3/2011 | Becker |
| 2011/0093069 A1 | 4/2011 | Goraltchouk et al. |
| 2011/0106249 A1 | 5/2011 | Becker |
| 2011/0117267 A1 | 5/2011 | Powell et al. |
| 2011/0196488 A1 | 8/2011 | Goraltchouk et al. |
| 2011/0196489 A1 | 8/2011 | Van Epps et al. |
| 2011/0276133 A1 | 11/2011 | Liu et al. |
| 2011/0276134 A1 | 11/2011 | Manesis et al. |
| 2011/0278755 A1 | 11/2011 | Liu et al. |
| 2011/0282444 A1 | 11/2011 | Liu et al. |
| 2011/0309541 A1 | 12/2011 | Thompson et al. |
| 2011/0313073 A1 | 12/2011 | Goraltchouk et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077891 A1 | 3/2012 | Liu et al. |
| 2012/0101574 A1 | 4/2012 | Goraltchouk et al. |
| 2012/0245685 A1 | 9/2012 | Yu |
| 2012/0321777 A1 | 12/2012 | Stroumpoulis et al. |
| 2013/0013062 A1 | 1/2013 | Thompson et al. |
| 2013/0023987 A1 | 1/2013 | Liu et al. |
| 2013/0032962 A1 | 2/2013 | Liu et al. |
| 2013/0053956 A1 | 2/2013 | Powell et al. |
| 2013/0158657 A1 | 6/2013 | Nofrey et al. |
| 2013/0209661 A1 | 8/2013 | Goraltchouk et al. |
| 2013/0245148 A1 | 9/2013 | Thompson et al. |
| 2013/0302511 A1 | 11/2013 | Goraltchouk et al. |
| 2013/0310934 A1 | 11/2013 | Van Epps et al. |

FOREIGN PATENT DOCUMENTS

| | | |
|---|---|---|
| EP | 0522585 | 1/1993 |
| EP | 1532942 | 5/2005 |
| JP | 2003-062062 | 4/2003 |
| JP | 2007-029717 | 8/2007 |
| WO | WO 98/10803 | 3/1998 |
| WO | WO 00/24437 | 5/2000 |
| WO | WO 2004/037318 | 5/2004 |
| WO | WO 2004/062531 | 7/2004 |
| WO | 2006/133366 | 12/2006 |
| WO | WO 2009/061672 | 5/2009 |
| WO | WO 2009/110917 | 9/2009 |
| WO | WO 2011/094155 | 8/2011 |
| WO | WO 2011/097499 | 8/2011 |

OTHER PUBLICATIONS

Inamed Aesthetics Brochure, Directions for Use Style 410 Silicone-Filled Breast Implants (2003).

Ma, Peter, "Scaffolds for tissue fabrication", Materials Today, 2004, 7, 30-40.

Mikes, Antonius et al., "Formation of Highly Porous Biodegradable Scaffolds for Tissue Engineering", Electronic Journal of Biotechnology. 2000, 3(2), 114-119.

Minami, Eliza et al., "The Composition and Behavior of Capsules Around Smooth and Textured Breast Implants in Pigs", Plastic and Reconstructive Surgery, 2006, 118940, 874-884.

Murphy, William et al., "Salt Fusion: An Approach to Improve Pore Interconnectivity Within Tissue Engineering Scaffolds", Tissue Engineering, vol. 8, Iss. 1, 2004.

Wei, Guobao et al., "Macroporous and Nanofibers Polymer Scaffolds and Polymer/bone-like Apatite Composite Scaffolds Generated by Sugar Spheres", Journal of Biomedical Materials Research Part A, 2006, 306-315.

Zhang, Yuan et al., "Macroporous Alumina Monoliths Prepared by Filling Polymer Foams With Alumina Hydrosols", J. Mater Sci., 44, 931-938 (2009).

* cited by examiner

POROUS MATERIALS, METHODS OF MAKING AND USES

This application claims priority to U.S. Patent Application No. 61/387,074, filed Sep. 28, 2010, the entire of disclosure of which is incorporated herein by this reference.

Polyurethanes are a class of compounds formed by reacting a polyol with a diisocyanate or a polymeric; isocyanate in the presence of suitable catalysts and additives. The structural geometry enables this highly durable material to be produced with varying density (such as, e.g., 6 kg/m3 to about 1,200 kg/m3) and flexible (flexible, semi-rigid and rigid), making polyurethane foam an ideal candidate for a wide variety of uses in both industrial and household applications. For example, flexible polyurethane foam may be produced in a variety of shapes and firmnesses useful as cushion underlay for carpets; as upholstery padding for furniture and vehicle interior components like seats, headrests, armrests, roof liners, dashboards, and instrument panels; as material for pillows, mattress bedding, toppers, and cores; as sponges; as mid- and outsoles of footwear; as vehicle fascia and other exterior parts; as fabric coatings as synthetic; fibers; as packaging material; as integral skin form for vehicle interiors; and as sound-deadening material. As another example, polyurethane foam may be produced as a rigid and light weight material useful in the manufacturing of insulating material such as, e.g., panel or spray insulation in buildings, water heaters, refrigerated transport, and commercial and residential refrigeration. Rigid polyurethane foams are also used in the manufacture of structural components, simulated wood, and flotation devices like boats, surfboards and life preservers. As yet another example, polyurethane foam may be produced having a wide variety of pore sizes useful in the manufacture of cleaning material such as, e.g., wipes, swabs, and abrasives; and filtration materials for air and/or liquid filtration.

Despite its immense versatility, there are several disadvantages associated with polyurethane foams that limit the scope of its applicability and usefulness. For example, polyurethane is unstable in the presence of chemicals (like acids, bases, and metal salts), oxidation, UV light, thermal, radiation, and. In addition, depending on its formulation, polyurethane absorbs a large range of organic solvents (like NMP, DMSO, DCM, xylene, hexane, dioxane, and acetone) causing deformation of its structure due to swelling. Further, degradation of polyurethane produces toxic byproducts that are harmful to organisms and the environment.

All of these disadvantages have an impact on polyurethane's performance range, for example, its use as filtration materials in applications involving solvents, acids, bases, and/or metal salts; its use as insulation materials in applications that also comprise solvents, acids, and/or bases; its use as materials in environmentally harsh applications where there is exposure to oxidation, metal salts, high UV, and/or radiation; its use as a biomedical material, like a component of a medical device, scaffolds (templates) for tissue engineering/regeneration, wound dressings, drug release matrixes, membranes for separations and filtration, sterile filters, artificial kidneys, absorbents, hemostatic devices, where biocompatibility and resistance to biodegradation are important.

SUMMARY

The present specification discloses novel porous materials. In one aspect of the invention, such materials may have a structural geometry substantially similar to polyurethane-based materials but with improved or different acid stability/resistance, base stability/resistance, chemical stability/resistance, thermal stability/resistance, oxidation stability/resistance, UV light stability/resistance, biocompatibility, biodegradation resistance, increased gas permeability, and/or increased range of mechanical properties, relative to polyurethane-based materials. As such, the disclosed porous materials are not only useful in all applications currently fulfilled by polyurethane-based materials, but also in many additional applications not suitable for polyurethane-based materials. For example, the porous materials disclosed herein can be used in a filter for separating or cleaning material present in a chemically aggressive environment, as a component of a medical device where biocompatibility and/or biostability are desired, as a material, or component thereof, exposed to chemical, oxidative, UV light, thermal and/or radiation environment that would destabilize and/or degrade a polyurethane-based material.

Thus, aspects of the present specification disclose a porous material comprising a matrix defining an array of interconnected pores. The matrix material can be a thermoset polymer, a thermoplastic polymer, an elastomer or a thermoplastic elastomer.

Other aspects of the present specification disclose a method of forming a porous material, the method comprising the steps of: a) coating porogens with a matrix material base to form a matrix material-coated porogen mixture; b) treating the matrix material-coated porogen mixture to form a porogen scaffold comprising fused porogens and cured or harden matrix material; and c) removing the porogen scaffold, wherein porogen scaffold removal results in a porous material, the porous material comprising a matrix defining an array of interconnected pores. The matrix material can be a thermoset polymer, a thermoplastic polymer, an elastomer or a thermoplastic elastomer.

Yet other aspects of the present specification disclose a porous material comprising a matrix defining an array of interconnected pores, wherein the porous material is made by the method comprising the steps of: a) coating porogens with a matrix material base to form a matrix material-coated porogen mixture; b) treating the matrix material-coated porogen mixture to form a porogen scaffold comprising fused porogens and cured or harden matrix material; and c) removing the porogen scaffold, wherein porogen scaffold removal results in a porous material, the porous material comprising a matrix defining an array of interconnected pores. The matrix material can be a thermoset polymer, a thermoplastic polymer, an elastomer or a thermoplastic elastomer.

Further aspects of the present specification disclose a method for making a molded article or device having a porous surface, the method comprising the step of: a) coating a mold or mandrel with a matrix material base; b) curing the matrix material base to form a base layer; c) coating the cured base layer with a matrix material base; d) coating the matrix material base with porogens to form a matrix material-coated porogen mixture; e) treating the matrix material-coated porogen mixture to form a porogen scaffold comprising fused porogens and cured matrix material base; and f) removing the porogen scaffold, wherein porogen scaffold removal results in a porous material, the porous material comprising a matrix defining an array of interconnected pores. In this method steps (c) and (d) can be repeated multiple times until the desired thickness of the matrix material layer is achieved. The matrix material can be a thermoset polymer, an elastomer or a thermoplastic elastomer.

In another aspect of the invention, an article of manufacture is provided, generally comprising a porous silicone elastomeric material made by the methods disclosed herein.

Porous materials of the present invention can be used in numerous and varied applications. In the biomedical field, porous materials of the invention can be used as a matrix for tissue engineering/regeneration, wound dressings, drug release matrices, membranes for separations and filtration, sterile filters, artificial kidneys, absorbents, hemostatic devices, and the like. In various industrial and household applications, porous materials of the invention can be used as insulating materials, packaging materials, impact absorbers, liquid or gas absorbents, wound dressings, personal hygiene products, such as but not limited to, cleaning and cleansing pads, wipes and swabs, deodorant, disposable towels, dry shampoo, facial tissues, handkerchiefs, hygiene wipes, paper towels, shaving brushes, tampons, towels, underarm liners, washing mitts, and wet wipes, membranes, filters and so forth.

DETAILED DESCRIPTION

Figure 1A:
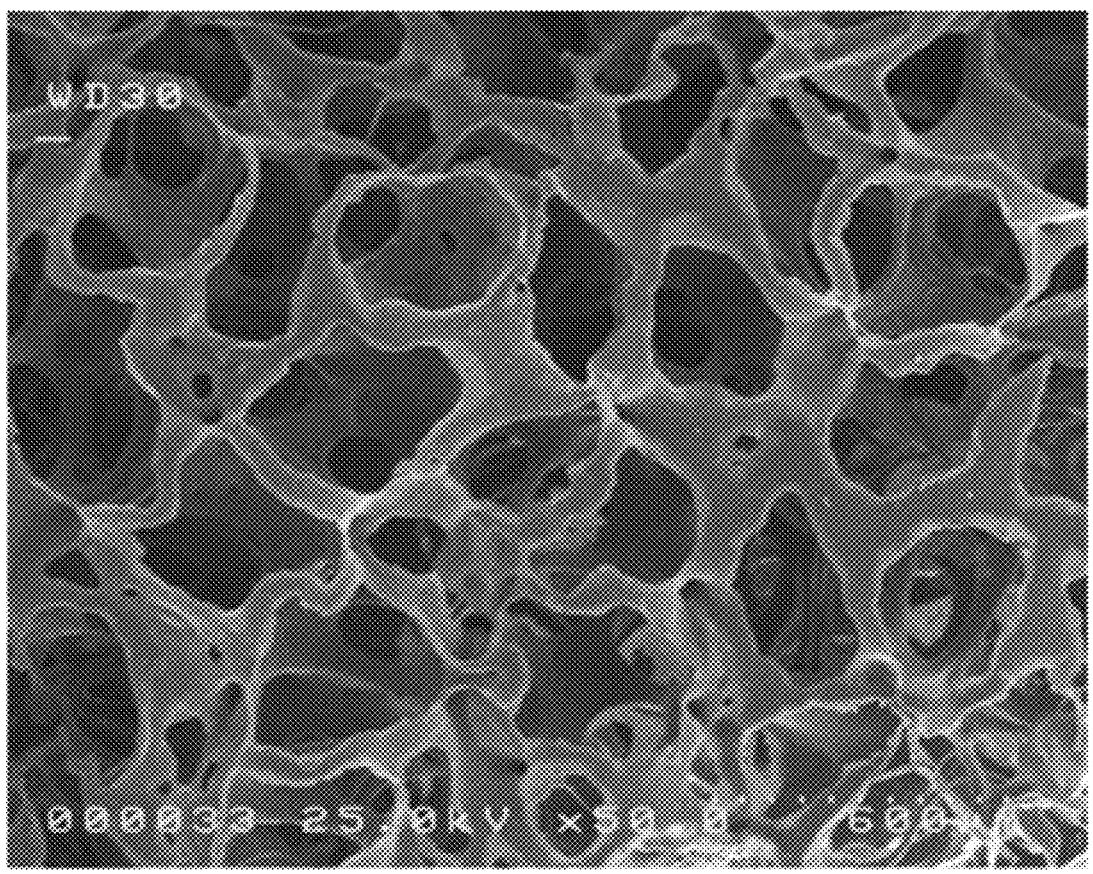
FIG. 1A is scanning electron micrograph image at 50× magnification of a material made in accordance with a method of the present invention.

The present specification discloses, in part, a porous material. A porous material disclosed herein can be made from any flowable or dissolvable matrix material that can be applied using the methods disclosed herein, Non-limiting examples of a flowable or dissolvable matrix material include thermoset polymers, thermoplastic polymers, elastomers, thermoplastic elastomers, or combinations thereof. A matrix material may comprise homopolymers or copolymers that are degradable, substantially non-degradable, or non-degradable. A matrix material useful in making the porous material disclosed herein may comprise block copolymers, random copolymers, alternating copolymers, graft copolymers, and/or mixtures thereof of thermoset polymers, thermoplastic polymers, elastomers, thermoplastic elastomers having an isotactic, syndiotactic or atactic organization. Isotactic polymers have all substituents located on the same side of the polymer backbone; the polymer comprises 100% meso diads. Syndiotactic polymers or syntactic polymers comprise have substituents in alternate positions along the chain; the polymer comprises 100% of racemic diads. Atactic polymers have substituents placed randomly along the chain; the polymer comprises between 1 and 99% meso diads. Such matrix materials include, for example carbon-based polymers, fluorocarbon-based polymers, and silicone-based polymers, including, without limitation, polyolefins, polyacrylates, fluoropolymers, polysiloxanes, polyesters, polyethers, polyethers, polycarbonates, polyamides, polyanhydrides, polyorthoesters, polyurethanes, polyureas, polysaccharides, polyalkanes, polyalkenes, polyalkynes, nitriles, and fluorosilicones.

The present specification discloses, in part, a thermoset polymer. As used herein, the term "thermoset" or "thermoset polymer" refers to a material that irreversibly hardens (i.e., sets) into a given shape, generally through a curing process. A thermoset polymer may comprise homopolymers or copolymers that are degradable, substantially non-degradable, or non-degradable. A thermoset polymer useful in making the porous material disclosed herein may comprise block copolymers, random copolymers, alternating copolymers, graft copolymers, and/or mixtures thereof. Thermoset polymers outperform other materials (such as thermoplastics, see below) in a number of areas, including mechanical properties, chemical resistance, thermal stability, and overall durability. Thermoplastics include, without limitation, thermoset elastomers including carbon-based thermoset elastomers, fluorocarbon-based thermoset elastomers and silicone-based thermoset elastomers; formaldehyde-based thermoset polymers like phenol-formaldehyde, urea-formaldehyde, melamine formaldehyde; poly(ester)-based thermoset polymers; poly (epoxide)-based thermoset polymers; poly(imide)-based thermoset polymers; and poly(cyanurate)-based thermoset polymers.

The present specification discloses, in part, a thermoplastic polymer. As used herein, the term "thermoplastic", "thermoplastic polymer", or "thermosoftening plastic" refers to a material that softens and becomes fluid when heated and which hardens or freezes to a very glassy state when cooled sufficiently. Thermoplastics are elastic and flexible above a glass transition temperature Tg, the midpoint of a temperature range. Below a second, higher melting temperature, Tm, also the midpoint of a range, most thermoplastics have crystalline regions alternating with amorphous regions in which the chains approximate random coils. The amorphous regions contribute elasticity and the crystalline regions contribute strength and rigidity. Above Tm all crystalline structure disappears and the chains become randomly inter dispersed. As the temperature increases above Tm, viscosity gradually decreases without any distinct phase change. During processing, thermoplastic pellets are heated to a fluid state that allows the material to be injected under pressure from a heated cavity into a cool mold. As the material cools, the thermoplastic will harden in the shape of the mold. However, no cross-links are formed as with a thermoset polymer (i.e., no curing). Thermoplastic polymers differ from thermosetting polymers in that the changes seen are purely physical and, with the reapplication of heat, wholly reversible. As such, thermoplastics can be reprocessed many times through a cycle of remelting and remolding. Most thermoplastics are high-molecular-weight polymers whose chains associate through weak Van der Waals forces; stronger dipole-dipole interactions and hydrogen bonding; or even stacking of aromatic rings. Thermoplastics include, e.g., amorphous thermoplastics, semi-crystalline thermoplastics, crystalline thermoplastics, and elastomeric and include, without limitation, poly(aryletherketone) (PAEK), poly(butylene terephthalate) (PBT), poly (butyrate), poly(ether ether ketone) (PEEK), poly(etherimide) (PEI), poly(2-hydroxyethyl methacrylate) (pHEMA), poly(isocyanurate) (PIR), poly(methyl methacrylate) (PMMA), poly(oxymethylene) (POM); poly(phenylsulfone) (PPSF), poly(styrene) (PS), poly(trimethylene terephthalate) (PTT), poly(urea) (PU); poly(amide)-based thermoplastics like aliphatic poly(amides), poly(phthalamides) (PPA), and aramides (aromatic poly(amides)); poly(carbonate)-based thermoplastics; poly(ester)-based thermoplastics like poly (ethylene) naphthalate (PEN), and poly(ethylene terephthalate) (PET); poly(olefin)-based thermoplastics like poly(ethylene) (PE), poly(propylene) (PP), poly(propylene carbonate) (PPC), poly(methylpentene) (PMP), and poly (butene-1) (PB-1); poly(stannane)-based thermoplastics; poly(sulfone)-based thermoplastics; poly(vinyl)-based thermoplastics like poly(vinyl chloride) (PVC), poly(vinylidene fluoride) (PVDF), poly(vinyl fluoride) (PVF), poly(vinyl nitrate) (PVN), and poly-(4-vinylphenol) (PVP); and cellulose-based thermoplastic like cellulose ester-based thermoplastics and cellulose ether-based thermoplastics.

The present specification discloses, in part, a fluoropolymer. As used herein, the term "fluoropolymer" refers to a fluorocarbon-based polymer with multiple strong carbon-fluorine bonds characterized by a high resistance to solvents, acids, and bases. Fluoropolymers include, without limitation, poly(vinyl fluoride) (PVF), poly(vinylidene fluoride) (PVDF), poly(tetrafluoroethylene) (PTFE), poly(chlorotrifluoroethylene) (PCTFE), perfluoroalkoxy (PFA), fluorinated ethylene-propylene (FEP), polyethylenetetrafluoroethylene (ETFE), poly(ethylenechlorotrifluoroethylene) (ECTFE), perfluoropolyether (PFPE) and fluoroelastomers.

The present specification discloses, in part, an elastomer. As used herein, the term "elastomer" or "elastic polymer" is synonymous with "thermoset elastomer" refers to an amorphous polymer that exists above its glass transition temperature (TO at ambient temperatures, thereby conferring the property of viscoelasticity so that considerable segmental motion is possible. Elastomers include, without limitation, carbon-based elastomers, silicone-based elastomers, thermoset elastomers, and thermoplastic elastomers. As used herein, the term "ambient temperature" refers to a temperature of about 18° C. to about 22° C. Elastomers, either naturally-occurring or synthetically-made, comprise monomers commonly made of carbon, hydrogen, oxygen, and/or silicone which are linked together to form long polymer chains. Elastomers are typically covalently cross-linked to one another, although non-covalently cross-linked elastomers are known. An elastomer may comprise homopolymers or copolymers that are degradable, substantially non-degradable, or non-degradable. An elastomer useful in making the porous material disclosed herein may comprise block copolymers, random copolymers, alternating copolymers, graft copolymers, and/or mixtures thereof. Unlike other polymers classes, an elastomer can be stretched many times its original length without breaking by reconfiguring themselves to distribute an applied stress, and the cross-linkages ensure that the elastomers will return to their original configuration when the stress is removed. Elastomers can be a non-medical grade elastomer or a medical grade elastomer, Medical grade elastomers are typically divided into three categories: non-implantable, short term implantable and long-term implantable. Exemplary elastomers include, without limitation, bromo isobutylene isoprene (BUR), polybutadiene (BR), chloro isobutylene isoprene (CHR), polychloroprene (CR), chlorosulphonated polyethylene (CSM), diphenylsiloxane (DPS), ethylene propylene (EP), ethylene propylene diene monomer (EPDM), fluorinated hydrocarbon (FKM), fluoro silicone (FVQM), hydrogenated nitrile butadiene (HNBR), polyisoprene (IR), isobutylene isoprene butyl (IIR), methyl vinyl silicone (MVQ), nitrile, acrylonitrile butadiene (NBR), polyurethane (PU), styrene butadiene (SBR), styrene ethylene/butylene styrene (SEBS), polydimethylsiloxane (PDMS), polysiloxane (Si), acrylonitrile butadiene carboxy monomer (XNBR), and polyolefin elastomers like polyisobutylene (RB), ethylene propylene rubber (EPR), ethylene propylene diene monomer (EPDM).

The present specification discloses, in part, an elastomer that is a fluorocarbon-based elastomer. As used herein, the term "fluorocarbon-based elastomer" refers to any fluorocarbon containing elastomer, such as, e.g., fluoro-elastomers (FKM), perfluoro-elastomers (FFKM) and tetrafluoro-ethylene/propylene elastomers (FEPM).

The present specification discloses, in part, an elastomer that is a silicone-based elastomer. In some embodiments, materials are provided which are substantially entirely silicone. As used herein, the term "scone-based elastomer" refers to any silicone containing elastomer, such as, e.g., methyl vinyl scone, polydimethylsiloxane, or polysiloxane. A scone-based elastomer can be a high temperature vulcanization (HTV) silicone or a room temperature vulcanization (RTV). A silicone-based elastomer can be a non-medical grade silicone-based elastomer or a medical grade silicone-based elastomer. As used herein, the term "medical grade silicone-based elastomer" refers to a silicone-based elastomer approved by the U.S. Pharmacopeia (USP) as at least Class V. Medical grade silicone-based elastomers are typically divided into three categories: non-implantable, short term implantable and long-term implantable.

Thus, in an embodiment, an elastomer is a medical grade elastomer. In aspects of this embodiment, a medical grade elastomer is, e.g., a medical grade carbon-based elastomer, a medical grade silicone-based elastomer, a medical grade thermoset elastomer, or a medical grade thermoplastic elastomer. In other aspects of this embodiment, an elastomer is, e.g., a medical grade, long-term implantable, carbon-based elastomer, a medical grade, long-term implantable, silicone-based elastomer, a medical grade, long-term implantable, thermoset elastomer, or a medical grade, long-term implantable, thermoplastic elastomer. In still other aspects, a medical grade elastomer is, e.g., a medical grade bromo isobutylene isoprene, a medical grade polybutadiene, a medical grade chloro isobutylene isoprene, a medical grade polychloroprene, a medical grade chlorosulphonated polyethylene, a medical grade ethylene propylene, a medical grade ethylene propylene diene monomer, a medical grade fluorinated hydrocarbon, a medical grade fluoro silicone, a medical grade hydrogenated nitrile butadiene, a medical grade polyisoprene, a medical grade isobutylene isoprene butyl, a medical grade methyl vinyl silicone, a medical grade acrylonitrile butadiene, a medical grade polyurethane, a medical grade styrene butadiene, a medical grade styrene ethylene/butylene styrene, a medical grade polydimethylsiloxane, a medical grade polysiloxane, or a medical grade acrylonitrile butadiene carboxy monomer.

In another embodiment, an elastomer is a silicone-based elastomer. In an aspect of this embodiment, a silicone-based elastomer is a medical grade silicone-based elastomer. In aspects of this embodiment, a medical grade silicone-based elastomer is, e.g., at least a USP Class V silicone-based elastomer, at least a USP Class VI silicone-based elastomer, or USP Class VII silicone-based elastomer. In yet other aspects, a medical grade silicone-based elastomer is a long-term implantable silicone-based elastomer. In yet other aspects, a medical grade silicone-based elastomer is, e.g., a medical grade, long-term implantable, methyl vinyl silicone, a medical grade, long-term implantable, polydimethylsiloxane, or a medical grade, long-term implantable, polysiloxane.

The present specification discloses, in part, a thermoplastic elastomer. As used herein, the term "thermoplastic elastomer" or "thermoplastic rubber" refers to a material comprising a class of copolymers or a physical mix of polymers of a plastic and an elastomer that exhibit both thermoplastic and elastomeric properties. The principal difference between thermoset elastomers and thermoplastic elastomers is the type of crosslinking bond in their structures. In fact, crosslinking is a critical structural factor that contributes to impart high elastic properties. The crosslink in thermoset polymers is a covalent bond created during the vulcanization process. On the other hand, the crosslink in thermoplastic elastomer polymers is a weaker dipole or hydrogen bond or takes place in one of the phases of the material. A thermoplastic elastomer combines the elastomer-like properties of a thermoset elastomer and the processing characteristics of a thermoplastic. The TPE achieves this blend because it is composed of two regions (or phases): soft phases (cured thermoset rubber particles) dispersed within hard phases (the thermoplastic portion). Be aware that the physical, chemical, and thermal limits of both phases will determine the overall limits for the TPE. Because it is a blended material, a TPE is also considerably more expensive than a simpler thermoset material. Thermoplastic elastomers include, without limitation, styrenic block copolymers, elastomeric alloys, thermoplastic polyurethanes, thermoplastic polyester elastomers copolymers, polyolefin blends, thermoplastic polyester blends, and thermoplastic polyamides blends. Non-limiting examples, include, ethylene-vinyl acetate (EVA), copolymers of polypropylene and ethylene propylene diene monomer (EPDM) elastomer, copolymers of polystyrene and polybutadiene, and copolymers of polystyrene and polyisoprene.

Elastomers have the property of viscoelasticity. Viscoelasticity is the property of materials that exhibit both viscous and elastic characteristics when undergoing deformation. Viscous materials resist shear flow and strain linearly with time when a stress is applied. Elastic materials strain instantaneously when stretched and just as quickly return to their original state once the stress is removed. Viscoelastic materials have elements of both of these properties and, as such, exhibit time dependent strain. A viscoelastic material has the following properties: 1) hysteresis, or memory, is seen in the stress-strain curve; 2) stress relaxation occurs: step constant strain causes decreasing stress; and 3) creep occurs: step constant stress causes increasing strain. The viscoelasticity of elastomers confer a unique set of properties involving elongation, tensile strength, shear strength compressive modulus, and hardness that distinguish elastomers from other classes of polymers.

Selection of a particular matrix material is within the knowledge level of a person of ordinary skill and will depend on the specific properties and characteristics desired of the porous material. For example, where the porous material is a component of an implantable medical device, the porous material will typically comprise a biocompatible, substantially non-degradable silicone-based elastomer. As another example, where the porous material is used as a component of an insulating application, the porous material will typically comprise a poly(styrene)-based low thermal conductivity thermoset polymer. As yet another example, where the porous material is a component of a filtration device for chemically aggressive or harsh applications, the porous material will typically comprise a fluoropolymer thermoset. As yet another example, where the porous material is a component of a light weight armor, the porous material will typically comprise a silicone-based elastomer, a fluorosilicone-based elastomer, or a fluoropolymer thermoset.

The present specification discloses, in part, a porous material comprising a matrix defining an array of interconnected pores. As used herein, the term "matrix defining an array of interconnected pores" or "matrix material defining an array of interconnected pores" is synonymous with "cured matrix" or "cured matrix material" and refers to a three-dimensional structural framework composed of a material, such as, e.g. a thermoset polymer, an elastomer, or a thermoplastic elastomer in its cured state or a material, such as, e.g., a thermoplastic polymer in its harden or solid state.

A porous material comprising a matrix defining an array of interconnected pores may exhibit high resistance to deformation. Resistance to deformation is the ability of a material to maintain its original form after being exposed to stress, and can be calculated as the original form of the material ($L_O$), divided by the form of the material after it is released from a stress ($L_R$), and then multiplied by 100.

In an embodiment, a porous material comprising a matrix defining an array of interconnected pores exhibits high resistance to deformation. In aspects of this embodiment, a porous material disclosed herein exhibits resistance to deformation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a porous material disclosed herein exhibits resistance to deformation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a porous material disclosed herein exhibits resistance to deformation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a porous material disclosed herein exhibits resistance to deformation of, e.g., about 85% to about 100%, about 87% to about 100%, about 90% to about 100%, about 93% to about 100%, about 95% to about 100%, or about 97% to about 100%.

A porous material comprising a matrix defining an array of interconnected pores may exhibit high elastic elongation. Elongation is a type of deformation caused when a material stretches under a tensile stress. Deformation is simply a change in shape that anything undergoes under stress. The elongation property of a material can be expressed as percent elongation, which is calculated as the length of a material after it is stretched (L), divided by the original length of the material ($L_O$), and then multiplied by 100. In addition, this elastic elongation may be reversible. Reversible elongation is the ability of a material to return to its original length after being release for a tensile stress, and can be calculated as the original length of the material ($L_O$), divided by the length of the material after it is released from a tensile stress ($L_R$), and then multiplied by 100.

In an embodiment, a porous material comprising a matrix defining an array of interconnected pores exhibits high elastic elongation. In aspects of this embodiment, a porous material disclosed herein exhibits an elastic elongation of, e.g., about 50%, about 80%, about 100%, about 200%, about 300%, about 400%, about 500%, about 600%, about 700%, about 800%, about 900%, about 1000%, about 1100%, about 1200%, about 1300%, about 1400%, about 1500%, about 1600%, about 1700%, about 1800%, about 1900%, or about 2000%. In other aspects of this embodiment, a porous material disclosed herein exhibits an elastic elongation of, e.g., at least 50%, at least 80%, at least 100%, at least 200%, at least 300%, at least 400%, at least 500%, at least 600%, at least 700%, at least 800%, at least 900%, at least 1000%, at least 1100%, at least 1200%, at least 1300%, at least 1400%, at least 1500%, at least 1600%, at least 1700%, at least 1800%, at least 1900%, or at least 2000%. In yet other aspects of this embodiment, a porous material disclosed herein exhibits an elastic elongation of, e.g., at most 50%, at most 80%, at most 100%, at most 200%, at most 300%, at most 400%, at most 500%, at most 600%, at most 700%, at most 800%, at most 900%, at most 1000%, at most 1100%, at most 1200%, at most 1300%, at most 1400%, at most 1500%, at most 1600%, at most 1700%, at most 1800%, at most 1900%, or at most 2000%. In still aspects of this embodiment, a porous material disclosed herein exhibits an elastic elongation of, e.g., about 50% to about 600%, about 50% to about 700%, about 50% to about 800%, about 50% to about 900%, about 50% to about 1000%, about 80% to about 600%, about 80% to about 700%, about 80% to about 800%, about 80% to about 900%, about 80% to about 1000%, about 100% to about 600%, about 100% to about 700%, about 100% to about 800%, about 100% to about 900%, about 100% to about 1000%, about 200% to about 600%, about 200% to about 700%, about 200% to about 800%, about 200% to about 900%, or about 200% to about 1000%.

In another embodiment, a porous material comprising a matrix defining an array of interconnected pores exhibits reversible elongation. In aspects of this embodiment, a porous material disclosed herein exhibits a reversible elastic elongation of, e.g., about 100%, about 99%, about 98%, about 97%, about 96%, about 95%, about 94%, about 93%, about 92%, about 91%, about 90%, about 89%, about 88%, about 87%, about 86%, or about 85%. In other aspects of this embodiment, a porous material disclosed herein exhibits a reversible elastic elongation of, e.g., at least 99%, at least 98%, at least 97%, at least 96%, at least 95%, at least 94%, at least 93%, at least 92%, at least 91%, at least 90%, at least 89%, at least 88%, at least 87%, at least 86%, or at least 85%. In yet other aspects of this embodiment, a porous material disclosed herein exhibits a reversible elastic elongation of, e.g., at most 99%, at most 98%, at most 97%, at most 96%, at most 95%, at most 94%, at most 93%, at most 92%, at most 91%, at most 90%, at most 89%, at most 88%, at most 87%, at most 86%, or at most 85%. In still aspects of this embodiment, a porous material disclosed herein exhibits a reversible elastic elongation of, e.g., about 85% to about 100%, about 87% to about 100%, about 90% to about 100%, about 93% to about 100%, about 95% to about 100%, or about 97% to about 100%.

A porous material comprising a matrix defining an array of interconnected pores may exhibit low elastic modulus. Elastic modulus, or modulus of elasticity, refers to the ability of a material to resists deformation, or, conversely, an object's tendency to be non-permanently deformed when a force is applied to it. The elastic modulus of an object is defined as the slope of its stress-strain curve in the elastic deformation region: $\lambda$=stress/strain, where $\lambda$ is the elastic modulus in Pascal's; stress is the force causing the deformation divided by the area to which the force is applied; and strain is the ratio of the change caused by the stress to the original state of the object. Specifying how stresses are to be measured, including directions, allows for many types of elastic moduli to be defined. The three primary elastic moduli are tensile modulus, shear modulus, and bulk modulus.

Tensile modulus (E) or Young's modulus is an objects response to linear strain, or the tendency of an object to deform along an axis when opposing forces are applied along that axis. It is defined as the ratio of tensile stress to tensile strain. It is often referred to simply as the elastic modulus. The shear modulus or modulus of rigidity refers to an object's tendency to shear (the deformation of shape at constant volume) when acted upon by opposing forces. It is defined as shear stress over shear strain. The shear modulus is part of the derivation of viscosity. The shear modulus is concerned with the deformation of a solid when it experiences a force parallel to one of its surfaces while its opposite face experiences an opposing force (such as friction). The bulk modulus (K) describes volumetric elasticity or an object's resistance to uniform compression, and is the tendency of an object to deform in all directions when uniformly loaded in all directions. It is defined as volumetric stress over volumetric strain, and is the inverse of compressibility. The bulk modulus is an extension of Young's modulus to three dimensions.

In another embodiment, a porous material comprising a matrix defining an array of interconnected pores exhibits low tensile modulus. In aspects of this embodiment, a porous material disclosed herein exhibits a tensile modulus of, e.g., about 0.01 MPa, about 0.02 MPa, about 0.03 MPa, about 0.04 MPa, about 0.05 MPa, about 0.06 MPa, about 0.07 MPa, about 0.08 MPa, about 0.09 MPa, about 0.1 MPa, about 0.15 MPa, about 0.2 MPa, about 0.25 MPa, about 0.3 MPa, about 0.35 MPa, about 0.4 MPa, about 0.45 MPa, about 0.5 MPa, about 0.55 MPa, about 0.6 MPa, about 0.65 MPa, or about 0.7 MPa. In other aspects of this embodiment, a porous material disclosed herein exhibits a tensile modulus of, e.g., at most 0.01 MPa, at most 0.02 MPa, at most 0.03 MPa, at most 0.04 MPa, at most 0.05 MPa, at most 0.06 MPa, at most 0.07 MPa, at most 0.08 MPa, at most 0.09 MPa, at most 0.1 MPa, at most 0.15 MPa, at most 0.2 MPa, at most 0.25 MPa, at most 0.3 MPa, at most 0.35 MPa, at most 0.4 MPa, at most 0.45 MPa, at most 0.5 MPa, at most 0.55 MPa, at most 0.6 MPa, at most 0.65 MPa, or at most 0.7 MPa. In yet other aspects of this embodiment, a porous material disclosed herein exhibits a tensile modulus of, e.g., about 0.01 MPa to about 0.1 MPa, about 0.01 MPa to about 0.2 MPa, about 0.01 MPa to about 0.3 MPa, about 0.01 MPa to about 0.4 MPa, about 0.01 MPa to about 0.5 MPa, about 0.01 MPa to about 0.6 MPa, or about 0.01 MPa to about 0.7 MPa.

In another embodiment, a porous material comprising a matrix defining an array of interconnected pores exhibits low shear modulus. In aspects of this embodiment, a porous material disclosed herein exhibits a shear modulus of, e.g., about 0.1 MPa, about 0.2 MPa, about 0.3 MPa, about 0.4 MPa, about 0.5 MPa, about 0.6 MPa, about 0.7 MPa, about 0.8 MPa, about 0.9 MPa, about 1 MPa, about 1.5 MPa, about 2 MPa, about 2.5 MPa, or about 3 MPa. In other aspects of this embodiment, a porous material disclosed herein exhibits a shear modulus of, e.g., at most 0.1 MPa, at most 0.2 MPa, at most 0.3 MPa, at most 0.4 MPa, at most 0.5 MPa, at most 0.6 MPa, at most 0.7 MPa, at most 0.8 MPa, at most 0.9 MPa, at most 1 MPa, at most 1.5 MPa, at most 2 MPa, at most 2.5 MPa, or at most 3 MPa. In yet other aspects of this embodiment, a porous material disclosed herein exhibits a shear modulus of, e.g., about 0.1 MPa to about 1 MPa, about 0.1 MPa to about 1.5 MPa, about 0.1 MPa to about 2 MPa, about 0.1 MPa to about 2.5 MPa, or about 0.1 MPa to about 3 MPa.

In another embodiment, a porous material comprising a matrix defining an array of interconnected pores exhibits low bulk modulus. In aspects of this embodiment, a porous material disclosed herein exhibits a bulk modulus of, e.g., about 0.5 GPa, about 0.6 GPa, about 0.7 GPa, about 0.8 GPa, about 0.9 GPa, about 1 GPa, about 1.5 GPa, about 2 GPa, about 2.5 GPa, about 3 GPa, about 3.5 GPa, about 4 GPa, about 4.5 GPa, or about 5 GPa. In other aspects of this embodiment, a porous material disclosed herein exhibits a bulk modulus of, e.g., at most 0.5 GPa, at most 0.6 GPa, at most 0.7 GPa, at most 0.8 GPa, at most 0.9 GPa, at most 1 GPa, at most 1.5 GPa, at most 2 GPa, at most 2.5 GPa, at most 3 GPa, at most 3.5 GPa, at most 4 GPa, at most 4.5 GPa, or at most 5 GPa. In yet other aspects of this embodiment, a porous material disclosed herein exhibits a bulk modulus of, e.g., about 0.5 GPa to about 5 GPa, about 0.5 GPa to about 1 GPa, or about 1 GPa to about 5 GPa.

A porous material comprising a matrix material defining an array of interconnected pores may exhibit high tensile strength relative to other polymer classes. Other polymer classes include any other polymer not classified as a matrix material. Tensile strength has three different definitional points of stress maxima. Yield strength refers to the stress at which material strain changes from elastic deformation to plastic deformation, causing it to deform permanently. Ultimate strength refers to the maximum stress a material can withstand when subjected to tension, compression or shearing. It is the maximum stress on the stress-strain curve. Breaking strength refers to the stress coordinate on the stress-strain curve at the point of rupture, or when the material pulls apart.

In another embodiment, a porous material comprising a matrix defining an array of interconnected pores exhibits high yield strength relative to other polymer classes. In aspects of this embodiment, a porous material disclosed herein exhibits a yield strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material disclosed herein exhibits a yield strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material disclosed herein exhibits a yield strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material disclosed herein exhibits a yield strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In another embodiment, a porous material comprising a matrix defining an array of interconnected pores exhibits high ultimate strength relative to other polymer classes. In aspects of this embodiment, a porous material disclosed herein exhibits an ultimate strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material disclosed herein exhibits an ultimate strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material disclosed herein exhibits an ultimate strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material disclosed herein exhibits an ultimate strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

In another embodiment, a porous material comprising a matrix defining an array of interconnected pores exhibits high breaking strength relative to other polymer classes. In aspects of this embodiment, a porous material disclosed herein exhibits a breaking strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material disclosed herein exhibits a breaking strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material disclosed herein exhibits a breaking strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material disclosed herein exhibits a breaking strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

A porous material comprising a matrix defining an array of interconnected pores may exhibit low flexural strength relative to other polymer classes. Flexural strength, also known as bend strength or modulus of rupture, refers to an object's ability to resist deformation under load and represents the highest stress experienced within the object at its moment of rupture. It is measured in terms of stress.

In an embodiment, a porous material comprising a matrix defining an array of interconnected pores exhibits low flexural strength relative to other polymer classes. In aspects of this embodiment, a porous material disclosed herein exhibits a flexural strength of, e.g., about 1 MPa, about 5 MPa, about 10 MPa, about 20 MPa, about 30 MPa, about 40 MPa, about 50 MPa, about 60 MPa, about 70 MPa, about 80 MPa, about 90 MPa, about 100 MPa, about 200 MPa, about 300 MPa, about 400 MPa, about 500 MPa, about 600 MPa, about 700 MPa, about 800 MPa, about 900 MPa, about 1000 MPa, about 1500 MPa, or about 2000 MPa. In other aspects of this embodiment, a porous material disclosed herein exhibits a flexural strength of, e.g., at least 1 MPa, at least 5 MPa, at least 10 MPa, at least 20 MPa, at least 30 MPa, at least 40 MPa, at least 50 MPa, at least 60 MPa, at least 70 MPa, at least 80 MPa, at least 90 MPa, at least 100 MPa, at least 200 MPa, at least 300 MPa, at least 400 MPa, at least 500 MPa, at least 600 MPa, at least 700 MPa, at least 800 MPa, at least 900 MPa, at least 1000 MPa, at least 1500 MPa, or at least 2000 MPa. In yet other aspects of this embodiment, a porous material disclosed herein exhibits a flexural strength of, e.g., at most 1 MPa, at most 5 MPa, at most 10 MPa, at most 20 MPa, at most 30 MPa, at most 40 MPa, at most 50 MPa, at most 60 MPa, at most 70 MPa, at most 80 MPa, at most 90 MPa, at most 100 MPa, at most 200 MPa, at most 300 MPa, at most 400 MPa, at most 500 MPa, at most 600 MPa, at most 700 MPa, at most 800 MPa, at most 900 MPa, at most 1000 MPa, at most 1500 MPa, or at most 2000 MPa. In still other aspects of this embodiment, a porous material disclosed herein exhibits a flexural strength of, e.g., about 1 MPa to about 50 MPa, about 1 MPa to about 60 MPa, about 1 MPa to about 70 MPa, about 1 MPa to about 80 MPa, about 1 MPa to about 90 MPa, about 1 MPa to about 100 MPa, about 10 MPa to about 50 MPa, about 10 MPa to about 60 MPa, about 10 MPa to about 70 MPa, about 10 MPa to about 80 MPa, about 10 MPa to about 90 MPa, about 10 MPa to about 100 MPa, about 100 MPa to about 500 MPA, about 300 MPa to about 500 MPA, about 300 MPa to about 1000 MPa, about 500 MPa to about 1000 MPa, about 700 MPa to about 1000 MPa, about 700 MPa to about 1500 MPa, about 1000 MPa to about 1500 MPa, or about 1200 MPa to about 1500 MPa.

A porous material comprising a matrix defining an array of interconnected pores may exhibit high compressibility. Compressibility refers to the relative volume change in response to a pressure (or mean stress) change, and is the reciprocal of the bulk modulus.

In an embodiment, a porous material comprising a matrix defining an array of interconnected pores exhibits high compressibility. In aspects of this embodiment, a porous material disclosed herein exhibits a compressibility of, e.g., about 0.1 kPa, about 0.5 kPa, about 1 kPa, about 5 kPa, about 10 kPa, about 15 kPa, about 20 kPa, about 30 kPa, about 40 kPa, about 50 kPa, about 60 kPa, about 70 kPa, about 80 kPa, about 90 kPa, or about 100 kPa. In other aspects of this embodiment, a porous material disclosed herein exhibits a compressibility of, e.g., at least 0.1 kPa, at least 0.5 kPa, at least 1 kPa, at least 5 kPa, at least 10 kPa, at least 15 kPa, at least 20 kPa, at least 30 kPa, at least 40 kPa, at least 50 kPa, at least 60 kPa, at least 70 kPa, at least 80 kPa, at least 90 kPa, or at least 100 kPa. In yet other aspects of this embodiment, a porous material disclosed herein exhibits a compressibility of, e.g., at most 0.1 kPa, at most 0.5 kPa, at most 1 kPa, at most 5 kPa, at most 10 kPa, at most 15 kPa, at most 20 kPa, at most 30 kPa, at most 40 kPa, at most 50 kPa, at most 60 kPa, at most 70 kPa, at most 80 kPa, at most 90 kPa, or at most 100 kPa. In still other aspects of this embodiment, a porous material disclosed herein exhibits a compressibility of, e.g., about 0.1 kPa to about 100 kPa, about 0.5 kPa to about 100 kPa, about 1 kPa to about 100 kPa, about 5 kPa to about 100 kPa, about 10 kPa to about 100 kPa, about 1 kPa to about 30 kPa, about 1 kPa to about 40 kPa, about 1 kPa to about 50 kPa, or about 1 kPa to about 60 kPa.

A porous material comprising a matrix defining an array of interconnected pores may exhibit low hardness. Hardness refers to various properties of an object in the solid phase that gives it high resistance to various kinds of shape change when force is applied. Hardness can be measured using a durometer and expressed using a Shore A scale, a unitless value that ranges from zero to 100.

In an embodiment, a porous material comprising a matrix defining an array of interconnected pores exhibits low hardness. In aspects of this embodiment, a porous material disclosed herein exhibits a Shore A hardness of, e.g., about 5, about 10, about 15, about 20, about 25, about 30, about 35, about 40, about 45, about 50, about 55, or about 60. In other aspects of this embodiment, a porous material disclosed herein exhibits a Shore A hardness of, e.g., at least 5, at least 10, at least 15, at least 20, at least 25, at least 30, at least 35, at least 40, at least 45, at least 50, at least 55, or at least 60. In yet other aspects of this embodiment, a porous material disclosed herein exhibits a Shore A hardness of, e.g., at most 5, at most 10, at most 15, at most 20, at most 25, at most 30, at most 35, at most 40, at most 45, at most 50, at most 55, or at most 60. In still other aspects of this embodiment, a porous material disclosed herein exhibits a Shore A hardness of, e.g., about 5 to about 60, about 10 to about 50, about 15 to about 45, about 20 to about 40, or about 25 to about 35.

A porous material comprising a matrix defining an array of interconnected pores may exhibit low thermal conductivity. Thermal conductivity, k, refers to the property of a material that indicates its ability to conduct heat and is measured in watts per Kelvin per meter ($W \cdot K^{-1} \cdot m^{-1}$). Multiplied by a temperature difference (in K) and an area (in $m^2$), and divided by a thickness (in m) the thermal conductivity predicts the energy loss (in W) through a piece of material. The reciprocal of thermal conductivity is thermal resistivity, and is measured in Kelvin-meters per watt ($K \cdot m \cdot W^{-1}$). Thermal conductance refers to the quantity of heat that passes in unit time through a plate of particular area and thickness when its opposite faces differ in temperature by one Kelvin. For a plate of thermal conductivity k, area A and thickness L this is kA/L, measured in $W \cdot K^{-1}$ (equivalent to: W/° C.). The reciprocal of thermal conductance is thermal resistance [L/(kA)], and is measured in $K \cdot W^{-1}$ (equivalent to: ° C./W). Heat transfer coefficient (k/L), also known as thermal admittance, refers to the quantity of heat that passes in unit time through unit area of a plate of particular thickness when its opposite faces differ in temperature by one Kelvin, and is measured in $W \cdot K^{-1} \ m^{-2}$. The reciprocal of heat transfer coefficient is thermal insulance (L/k), and is measured in $K \cdot m^2 W^{-1}$.

In an embodiment, a porous material comprising a matrix defining an array of interconnected pores exhibits low thermal conductivity. In aspects of this embodiment, a porous material disclosed herein exhibits a thermal conductivity of, e.g., about 0.010 $Wm^{-1}K^{-1}$, about 0.025 $Wm^{-1}K^{-1}$, about 0.050 $Wm^{-1}K^{-1}$ about 0.075 $Wm^{-1}K^{-1}$, about 0.10 $Wm^{-1}K^{-1}$, about 0.25 $Wm^{-1}K^{-1}$, about 0.50 $Wm^{-1}K^{-1}$, about 0.75 $Wm^{-1}K^{-1}$, about 1.0 $Wm^{-1}K^{-1}$, about 2.5 $Wm^{-1}K^{-1}$, about 5.0 $Wm^{-1}K^{-1}$, about 7.5 $Wm^{-1}K^{-1}$, or about 10 $Wm^{-1}K^{-1}$. In other aspects of this embodiment, a porous material disclosed herein exhibits a thermal conductivity of, e.g., at most 0.010 $Wm^{-1}K^{-1}$, at most 0.025 $Wm^{-1}K^{-1}$, at most 0.050 $Wm^{-1}K^{-1}$, at most 0.075 $Wm^{-1}K^{-1}$, at most 0.10 $Wm^{-1}K^{-1}$, at most 0.25 $Wm^{-1}K^{-1}$, at most 0.50 $Wm^{-1}K^{-1}$, at most 0.75 $Wm^{-1}K^{-1}$, at most 1.0 $Wm^{-1}K^{-1}$, at most 2.5 $Wm^{-1}K^{-1}$, at most 5.0 $Wm^{-1}K^{-1}$, at most 7.5 $Wm^{-1}K^{-1}$, or at most 10 $Wm^{-1}K^{-1}$. In yet other aspects of this embodiment, a porous material disclosed herein exhibits a thermal conductivity of, e.g., about 0.010 $Wm^{-1}K^{-1}$ to about 0.10 $Wm^{-1}K^{-1}$, about 0.010 $Wm^{-1}K^{-1}$ to about 1.0 $Wm^{-1}K^{-1}$, about 0.010 $Wm^{-1}K^{-1}$ to about 10 $Wm^{-1}K^{-1}$, about 0.050 $Wm^{-1}K^{-1}$ to about 0.50 $Wm^{-1}K^{-1}$, about 0.050 $Wm^{-1}K^{-1}$ to about 5.0 $Wm^{-1}K^{-1}$, about 0.010 $Wm^{-1}K^{-1}$ to about 0.050 $Wm^{-1}K^{-1}$, about 0.025 $Wm^{-1}K^{-1}$ to about 0.075 $Wm^{-1}K^{-1}$, about 0.050 $Wm^{-1}K^{-1}$ to about 0.10 $Wm^{-1}K^{-1}$, about 0.075 $Wm^{-1}K^{-1}$ to about 0.25 $Wm^{-1}K^{-1}$, about 0.10 $Wm^{-1}K^{-1}$ to about 0.50 $Wm^{-1}K^{-1}$, about 0.25 $Wm^{-1}K^{-1}$ to about 0.75 $Wm^{-1}K^{-1}$, about 0.50 $Wm^{-1}K^{-1}$ to about 1.0 $Wm^{-1}K^{-1}$, about 0.75 $Wm^{-1}K^{-1}$ to about 2.5 $Wm^{-1}K^{-1}$, about 1.0 $Wm^{-1}K^{-1}$ to about 5.0 $Wm^{-1}K^{-1}$, about 2.5 $Wm^{-1}K^{-1}$ to about 7.5 $Wm^{-1}K^{-1}$, or about 5.0 $Wm^{-1}K^{-1}$ to about 10 $Wm^{-1}K^{-1}$.

A porous material comprising a matrix includes pores having a shape sufficient to enable the desired function of the porous material. Useful pore shapes include, without limitation, roughly spherical, perfectly spherical, dodecahedrons (such as pentagonal dodecahedrons), and ellipsoids. For example, in certain biomedical applications, the shape of the pores should be in a form sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the shape of the pores should be in a form that facilitates removal unwanted substances from the filtered material.

A porous material comprising a matrix includes pores having a roundness sufficient to enable the desired function of the porous material. As used herein, "roundness" is defined as $(6 \times V)/(\pi \times D^3)$, where V is the volume and D is the diameter. Any pore roundness is useful with the proviso that the pore roundness is sufficient to enable the desired function of the porous material. For example, in certain biomedical applications, pore roundness should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, pore roundness should be sufficient to facilitate removal unwanted substances from the filtered material.

A porous material comprising a matrix may be formed in such a manner that substantially all the pores in the matrix have a similar diameter. As used herein, the term "substantially", when used to describe pores, refers to at least 90% of the pores within the matrix such as, e.g., at least 95% or at least 97% of the pores. As used herein, the term "similar diameter", when used to describe pores, refers to a difference in the diameters of the two pores that is less than about 20% of the larger diameter. As used herein, the term "diameter", when used to describe pores, refers to the longest line segment that can be drawn that connects two points within the pore, regardless of whether the line passes outside the boundary of the pore. For example, in certain biomedical applications, pore diameter should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, pore diameter should be sufficient to facilitate removal unwanted substances from the filtered material.

A porous material comprising a matrix is formed in such a manner that the diameter of the connections between pores is sufficient to enable the desired function of the porous material. As used herein, the term "diameter", when describing the connection between pores, refers to the diameter of the cross-section of the connection between two pores in the plane normal to the line connecting the centroids of the two pores, where the plane is chosen so that the area of the cross-section of the connection is at its minimum value. As used herein, the term "diameter of a cross-section of a connection" refers to the average length of a straight line segment that passes through the center, or centroid (in the case of a connection having a cross-section that lacks a center), of the cross-section of a connection and terminates at the periphery of the cross-section. As used herein, the term "substantially", when used to describe the connections between pores refers to at least 90% of the connections made between each pore comprising the matrix, such as, e.g., at least 95% or at least 97% of the connections. For example, in certain biomedical applications, the diameter of the connections between pores should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the diameter of the connections between pores should be sufficient to facilitate removal unwanted substances from the filtered material.

Thus, in an embodiment, a porous material comprising matrix defining an array of interconnected pores includes pores having a roundness sufficient to enable the desired function of the porous material. In aspects of this embodiment, a porous material disclosed herein includes pores having a roundness of, e.g., about 0.1, about 0.2, about 0.3, about 0.4, about 0.5, about 0.6, about 0.7, about 0.8, about 0.9, or about 1.0. In other aspects of this embodiment, a porous material disclosed herein includes pores having a roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, a porous material disclosed herein includes pores having a roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, a porous material disclosed herein includes pores having a roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

In another embodiment, substantially all pores within a porous material comprising a matrix have a similar diameter sufficient to enable the desired function of the porous material. In aspects of this embodiment, at least 90% of all pores within a porous material comprising a matrix have a similar diameter, at least 95% of all pores within a porous material comprising a matrix have a similar diameter, or at least 97% of all pores within a porous material comprising a matrix have a similar diameter. In another aspect of this embodiment, difference in the diameters of two pores is, e.g., less than about 20% of the larger diameter, less than about 15% of the larger diameter, less than about 10% of the larger diameter, or less than about 5% of the larger diameter.

In another embodiment, a porous material comprising a matrix defining an array of interconnected pores includes pores having a mean diameter sufficient to enable the desired function of the porous material. In aspects of this embodiment, a porous material comprising a matrix includes pores having mean pore diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porous material disclosed herein includes pores having mean pore diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porous material disclosed herein includes pores having mean pore diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a porous material disclosed herein includes pores having mean pore diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porous material disclosed herein includes pores having mean pore diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a porous material disclosed herein includes pores having mean pore diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porous material disclosed herein includes pores having mean pore diameter in a range from, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porous material comprising a matrix defining an array of interconnected pores includes pores having a mean matrix strut thickness sufficient to enable the desired function of the porous material. In aspects of this embodiment, a porous material disclosed herein includes pores having a mean matrix strut thickness of, e.g., about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, or about 200 µm. In other aspects of this embodiment, a porous material disclosed herein includes pores having a mean matrix strut thickness of, e.g., at least 10 µm, at least 20 µm, at least 30 µm, at least 40 µm, at least 50 µm, at least 60 µm, at least 70 µm, at least 80 µm, at least 90 µm, at least 100 µm, at least 110 µm, at least 120 µm, at least 130 µm, at least 140 µm, at least 150 µm, at least 160 µm, at least 170 µm, at least 180 µm, at least 190 µm, or at least 200 µm. In yet other aspects of this embodiment, a porous material disclosed herein includes pores having a mean matrix strut thickness of, e.g., at most 10 µm, at most 20 µm, at most 30 µm, at most 40 µm, at most 50 µm, at most 60 µm, at most 70 µm, at most 80 µm, at most 90 µm, at most 100 µm, at most 110 µm, at most 120 µm, at most 130 µm, at most 140 µm, at most 150 µm, at most 160 µm, at most 170 µm, at most 180 µm, at most 190 µm, or at most 200 µm. In still aspects of this embodiment, a porous material disclosed herein includes pores having a mean matrix strut thickness of, e.g., about 50 µm to about 110 µm, about 50 µm to about 120 µm, about 50 µm to about 130 µm, about 50 µm to about 140 µm, about 50 µm to about 150 µm, about 60 µm to about 110 µm, about 60 µm to about 120 µm, about 60 µm to about 130 µm, about 60 µm to about 140 µm, about 70 µm to about 110 µm, about 70 µm to about 120 µm, about 70 µm to about 130 µm, or about 70 µm to about 140 µm.

In another embodiment, a porous material comprising a matrix defining an array of interconnected pores includes pores connected to a plurality of other pores. In aspects of this embodiment, a porous material disclosed herein comprises a mean pore connectivity, e.g., about two other pores, about three other pores, about four other pores, about five other pores, about six other pores, about seven other pores, about eight other pores, about nine other pores, about ten other pores, about 11 other pores, or about 12 other pores. In other aspects of this embodiment, a porous material disclosed herein comprises a mean pore connectivity, e.g., at least two other pores, at least three other pores, at least four other pores, at least five other pores, at least six other pores, at least seven other pores, at least eight other pores, at least nine other pores, at least ten other pores, at least 11 other pores, or at least 12 other pores. In yet other aspects of this embodiment, a porous material disclosed herein comprises a mean pore connectivity, e.g., at most two other pores, at most three other pores, at most four other pores, at most five other pores, at most six other pores, at most seven other pores, at most eight other pores, at most nine other pores, at most ten other pores, at most 11 other pores, or at most 12 other pores.

In still other aspects of this embodiment, a porous material disclosed herein includes pores connected to, e.g., about two other pores to about 12 other pores, about two other pores to about 11 other pores, about two other pores to about ten other pores, about two other pores to about nine other pores, about two other pores to about eight other pores, about two other pores to about seven other pores, about two other pores to about six other pores, about two other pores to about five other pores, about three other pores to about 12 other pores, about three other pores to about 11 other pores, about three other pores to about ten other pores, about three other pores to about nine other pores, about three other pores to about eight other pores, about three other pores to about seven other pores, about three other pores to about six other pores, about three other pores to about five other pores, about four other pores to about 12 other pores, about four other pores to about 11 other pores, about four other pores to about ten other pores, about four other pores to about nine other pores, about four other pores to about eight other pores, about four other pores to about seven other pores, about four other pores to about six other pores, about four other pores to about five other pores, about five other pores to about 12 other pores, about five other pores to about 11 other pores, about five other pores to about ten other pores, about five other pores to about nine other pores, about five other pores to about eight other pores, about five other pores to about seven other pores, or about five other pores to about six other pores.

In another embodiment, a porous material comprising a matrix defining an array of interconnected pores includes pores where the diameter of the connections between pores is sufficient to enable the desired function of the porous material. In aspects of this embodiment, a porous material disclosed herein includes pores where the diameter of the connections between pores is, e.g., about 10% the mean pore diameter, about 20% the mean pore diameter, about 30% the mean pore diameter, about 40% the mean pore diameter, about 50% the mean pore diameter, about 60% the mean pore diameter, about 70% the mean pore diameter, about 80% the mean pore diameter, or about 90% the mean pore diameter. In other aspects of this embodiment, a porous material disclosed herein includes pores where the diameter of the connections between pores is, e.g., at least 10% the mean pore diameter, at least 20% the mean pore diameter, at least 30% the mean pore diameter, at least 40% the mean pore diameter, at least 50% the mean pore diameter, at least 60% the mean pore diameter, at least 70% the mean pore diameter, at least 80% the mean pore diameter, or at least 90% the mean pore diameter. In yet other aspects of this embodiment, a porous material disclosed herein includes pores where the diameter of the connections between pores is, e.g., at most 10% the mean pore diameter, at most 20% the mean pore diameter, at most 30% the mean pore diameter, at most 40% the mean pore diameter, at most 50% the mean pore diameter, at most 60% the mean pore diameter, at most 70% the mean pore diameter, at most 80% the mean pore diameter, or at most 90% the mean pore diameter.

In still other aspects of this embodiment, a porous material disclosed herein includes pores where the diameter of the connections between pores is, e.g., about 10% to about 90% the mean pore diameter, about 15% to about 90% the mean pore diameter, about 20% to about 90% the mean pore diameter, about 25% to about 90% the mean pore diameter, about 30% to about 90% the mean pore diameter, about 35% to about 90% the mean pore diameter, about 40% to about 90% the mean pore diameter, about 10% to about 80% the mean pore diameter, about 15% to about 80% the mean pore diameter, about 20% to about 80% the mean pore diameter, about 25% to about 80% the mean pore diameter, about 30% to about 80% the mean pore diameter, about 35% to about 80% the mean pore diameter, about 40% to about 80% the mean pore diameter, about 10% to about 70% the mean pore diameter, about 15% to about 70% the mean pore diameter, about 20% to about 70% the mean pore diameter, about 25% to about 70% the mean pore diameter, about 30% to about 70% the mean pore diameter, about 35% to about 70% the mean pore diameter, about 40% to about 70% the mean pore diameter, about 10% to about 60% the mean pore diameter, about 15% to about 60% the mean pore diameter, about 20% to about 60% the mean pore diameter, about 25% to about 60% the mean pore diameter, about 30% to about 60% the mean pore diameter, about 35% to about 60% the mean pore diameter, about 40% to about 60% the mean pore diameter, about 10% to about 50% the mean pore diameter, about 15% to about 50% the mean pore diameter, about 20% to about 50% the mean pore diameter, about 25% to about 50% the mean pore diameter, about 30% to about 50% the mean pore diameter, about 10% to about 40% the mean pore diameter, about 15% to about 40% the mean pore diameter, about 20% to about 40% the mean pore diameter, about 25% to about 40% the mean pore diameter, or about 30% to about 40% the mean pore diameter.

The present specification discloses, in part, a porous material comprising a matrix defining an array of interconnected pores having a porosity sufficient to enable the desired function of the porous material. As used herein, the term "porosity" refers to the amount of void space in a porous material comprising a matrix. As such, the total volume of a porous material comprising a matrix disclosed herein is based upon the matrix space and the void space. For example, in certain biomedical applications, the porosity of the porous material should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the porosity of the porous material should be sufficient to facilitate removal unwanted substances from the filtered material.

In aspects of this embodiment, a porous material comprising a matrix defining an array of interconnected pores has a porosity of, e.g., about 40% of the total volume of a matrix, about 50% of the total volume of a matrix, about 60% of the total volume of a matrix, about 70% of the total volume of a matrix, about 80% of the total volume of a matrix, about 90% of the total volume of a matrix, about 95% of the total volume of a matrix, or about 97% of the total volume of a matrix. In other aspects of this embodiment, a porous material disclosed herein has a porosity of, e.g., at least 40% of the total volume of a matrix, at least 50% of the total volume of a matrix, at least 60% of the total volume of a matrix, at least 70% of the total volume of a matrix, at least 80% of the total volume of a matrix, at least 90% of the total volume of a matrix, at least 95% of the total volume of a matrix, or at least 97% of the total volume of a matrix. In yet other aspects of this embodiment, a porous material disclosed herein has a porosity of, e.g., at most 40% of the total volume of a matrix, at most 50% of the total volume of a matrix, at most 60% of the total volume of a matrix, at most 70% of the total volume of a matrix, at most 80% of the total volume of a matrix, at most 90% of the total volume of a matrix, at most 95% of the total volume of a matrix, or at most 97% of the total volume of a matrix. In yet other aspects of this embodiment, a porous material disclosed herein has a porosity of, e.g., about 40% to about 97% of the total volume of a matrix, about 50% to about 97% of the total volume of a matrix, about 60% to about 97% of the total volume of a matrix, about 70% to about 97% of the total volume of a matrix, about 80% to about 97% of the total volume of a matrix, about 90% to about 97% of the total volume of a matrix, about 40% to about 95% of the total volume of a matrix, about 50% to about 95% of the total volume of a matrix, about 60% to about 95% of the total volume of a matrix, about 70% to about 95% of the total volume of a matrix, about 80% to about 95% of the total volume of a matrix, about 90% to about 95% of the total volume of a matrix, about 40% to about 90% of the total volume of a matrix, about 50% to about 90% of the total volume of a matrix, about 60% to about 90% of the total volume of a matrix, about 70% to about 90% of the total volume of a matrix, or about 80% to about 90% of the total volume of a matrix.

The present specification discloses, in part, a porous material comprising a matrix defining an array of interconnected pores having a mean open pore value and/or a mean closed pore value sufficient to enable the desired function of the porous material. As used herein, the term "mean open pore value" or "mean open pore" refers to the average number of pores that are connected to at least one other pore present in the matrix. As used herein, the term "mean closed pore value" or "mean closed pore" refers to the average number of pores that are not connected to any other pores present in the matrix. For example, in certain biomedical applications, the array of interconnected pores should have a mean open pore value and/or a mean closed pore value sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the array of interconnected pores should have a mean open pore value and/or a mean closed pore value sufficient to facilitate removal unwanted substances from the filtered material.

In aspects of this embodiment, a porous material comprising a matrix defining an array of interconnected pores has a mean open pore value of, e.g., about 70%, about 75%, about 80%, about 85%, about 90%, about 95%, or about 97%. In other aspects of this embodiment, a porous material disclosed herein has a mean open pore value of, e.g., at least 70%, at least 75%, at least 80%, at least 85%, at least 90%, at least 95%, or at least 97%. In yet other aspects of this embodiment, a porous material disclosed herein has a mean open pore value of, e.g., at most 70%, at most 75%, at most 80%, at most 85%, at most 90%, at most 95%, or at most 97%. In still aspects of this embodiment, a porous material disclosed herein has a mean open pore value of, e.g., about 70% to about 90%, about 75% to about 90%, about 80% to about 90%, about 85% to about 90%, about 70% to about 95%, about 75% to about 95%, about 80% to about 95%, about 85% to about 95%, about 90% to about 95%, about 70% to about 97%, about 75% to about 97%, about 80% to about 97%, about 85% to about 97%, or about 90% to about 97%.

In another embodiment, a porous material comprising a matrix defining an array of interconnected pores has a mean closed pore value sufficient to enable the desired function of the porous material. In aspects of this embodiment, a porous material disclosed herein has a mean closed pore value of, e.g., about 5%, about 10%, about 15%, or about 20%. In other aspects of this embodiment, a porous material disclosed herein has a mean closed pore value of, e.g., about 5% or less, about 10% or less, about 15% or less, or about 20% or less. In yet other aspects of this embodiment, a porous material disclosed herein has a mean closed pore value of, e.g., about 5% to about 10%, about 5% to about 15%, or about 5% to about 20%.

The present specification discloses, in part, a porous material comprising a matrix defining an array of interconnected pores having a void space sufficient to enable the desired function of the porous material. As used herein, the term "void space" refers to actual or physical space in a porous material comprising a matrix. As such, the total volume of a porous material comprising a matrix disclosed herein is based upon the matrix space and the void space. For example, in certain biomedical applications, the void space should be sufficient to support aspects tissue growth into the array of interconnected pores, thereby supporting aspects of tissue growth such as, e.g., cell migration, cell proliferation, cell differentiation, nutrient exchange, and/or waste removal. As another example, in filtration applications, the void space should be sufficient to facilitate removal unwanted substances from the filtered material.

In aspects of this embodiment, a porous material comprising a matrix defining an array of interconnected pores has a void space of, e.g., about 50% of the total volume of a matrix, about 60% of the total volume of a matrix, about 70% of the total volume of a matrix, about 80% of the total volume of a matrix, about 90% of the total volume of a matrix, about 95% of the total volume of a matrix, or about 97% of the total volume of a matrix. In other aspects of this embodiment, a porous material disclosed herein has a void space of, e.g., at least 50% of the total volume of a matrix, at least 60% of the total volume of a matrix, at least 70% of the total volume of a matrix, at least 80% of the total volume of a matrix, at least 90% of the total volume of a matrix, at least 95% of the total volume of a matrix, or at least 97% of the total volume of a matrix. In yet other aspects of this embodiment, a porous material disclosed herein has a void space of, e.g., at most 50% of the total volume of a matrix, at most 60% of the total volume of a matrix, at most 70% of the total volume of a matrix, at most 80% of the total volume of a matrix, at most 90% of the total volume of a matrix, at most 95% of the total volume of a matrix, or at most 97% of the total volume of a matrix. In yet other aspects of this embodiment, a porous material disclosed herein has a void space of, e.g., about 50% to about 97% of the total volume of a matrix, about 60% to about 97% of the total volume of a matrix, about 70% to about 97% of the total volume of a matrix, about 80% to about 97% of the total volume of a matrix, about 90% to about 97% of the total volume of a matrix, about 50% to about 95% of the total volume of a matrix, about 60% to about 95% of the total volume of a matrix, about 70% to about 95% of the total volume of a matrix, about 80% to about 95% of the total volume of a matrix, about 90% to about 95% of the total volume of a matrix, about 50% to about 90% of the total volume of a matrix, about 60% to about 90% of the total volume of a matrix, about 70% to about 90% of the total volume of a matrix, or about 80% to about 90% of the total volume of a matrix.

A porous material comprising a matrix defining an array of interconnected pores generally has a low level of microporosity. As used herein, the term "microporosity" refers to a measure of the presence of small micropores within a porous material comprising a matrix itself (as opposed to the pores defined by a matrix). In some embodiments, all or substantially all of the micropores in a porous material disclosed herein are between about 0.1 µm and about 5 µm, such as between about 0.1 µm and about 3 µm or between about 0.1 µm and about 2 µm. The term "low level of microporosity" means that micropores represent less than 2% of the volume of a porous material disclosed herein, as measured by measuring the percentage void space in a cross-section through a matrix.

Figure 1B:
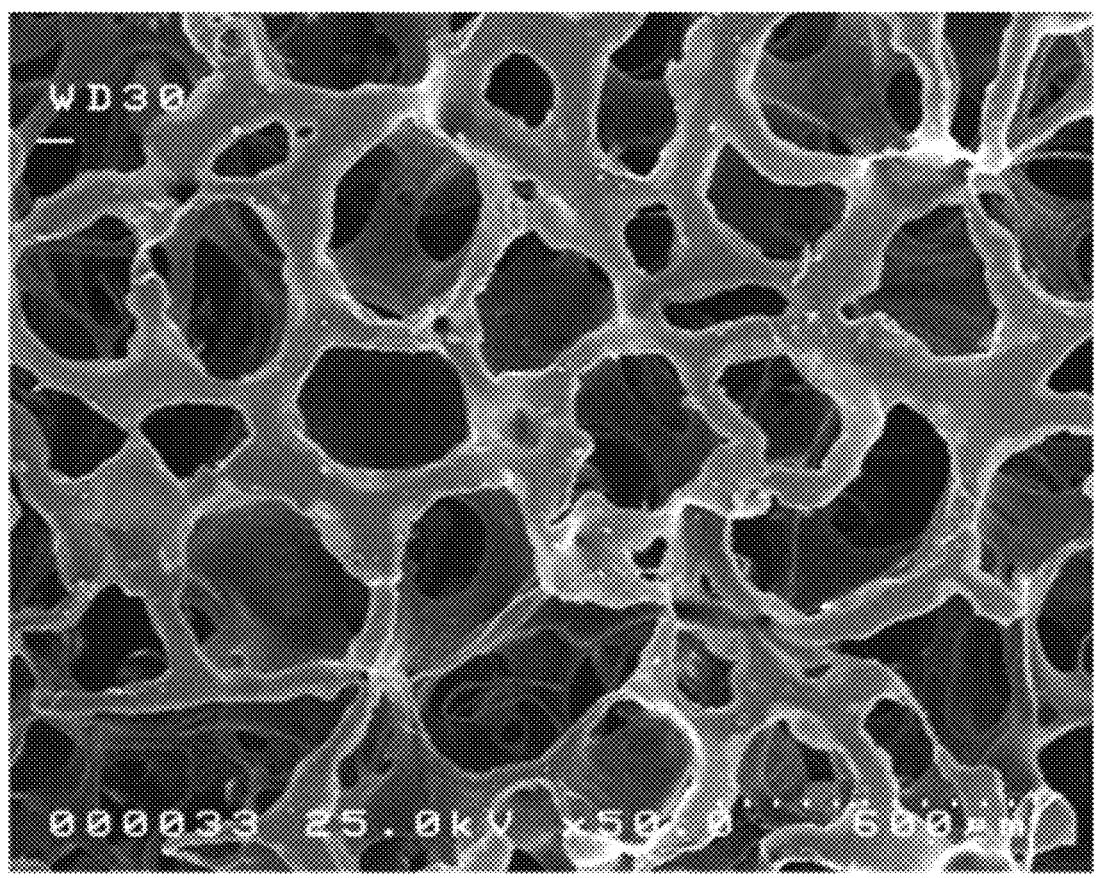
FIG. 1B is scanning electron micrograph image at 50× magnification of another material made in accordance with a method of the present invention.

The shape, roundness, and diameter of pores, the connections between pores, the total volume of the porous material, the void volume, and the matrix volume can all be assessed using scanning electron microscopy. See, e.g., FIGS. 1A and 1B.

The disclosed porous materials are not only useful in all applications currently fulfilled by polyurethane-based materials, but also in many additional applications not ideally suitable for polyurethane-based materials. Non-limiting examples of applications for the porous materials disclosed herein include cushion underlay for carpets; upholstery padding for furniture and vehicle interior components like seats, headrests, armrests, roof liners, dashboards, and instrument panels; material for pillows, mattress bedding, toppers, and cores; sponges; mid- and outsoles of footwear; vehicle fascia and other exterior parts; fabric coatings as synthetic fibers; packaging material; integral skin form for vehicle interiors; sound-deadening material; insulating material such as, e.g., panel or spray insulation in buildings, water heaters, refrigerated transport, and commercial and residential refrigeration; structural components; simulated wood; cleaning material such as, e.g., wipes, swabs, and abrasives; and filtration materials for air and/or liquid filtration; filters for separating or cleaning material present in a chemically aggressive environment; and light weight armor material.

The present specification discloses, in part, a porous material comprising a matrix defining an array of interconnected pores having a low thermal conductivity and/or high acoustic absorption. Such a porous material is useful in insulation materials such as, e.g., panel or spray insulation in buildings, water heaters, refrigerated transport, and commercial and residential refrigeration. Additionally, such a porous material may be insoluble or substantially insoluble in solvents, acids, and/or bases used during the application of the insulating material or exposed to once installed. An insulating material useful for thermal insulation will typically be made from a thermoplastic polymer, such as, e.g., polystyrene. The porous material may be made in sheet form typically from about 0.5 cm to about 10 cm in thickness with a porosity of about 70 to about 95% with at least partly open pores with interconnection diameter from approximately 1.0 µm to approximately 150 µm and a mean pore size of about 50 µm to about 800 µm.

The present specification discloses, in part, a porous material comprising a matrix defining an array of interconnected pores useful in the manufacturing of cleaning materials, such as, e.g., wipes, swabs, and abrasives, and including personal hygiene products. Such porous cleaning materials are typically designed for particular applications by optimizing absorption or the affinity of the polymer and porosity of the matrix for the material to be cleaned. For instance, for industrial cleaning, acidic aqueous solutions may be cleaned with a porous material comprising a lightly crosslinked polymer having basic functionalities on the backbone or pendants, such as lightly crosslinked chitosan or poly(ethyleneamine), which would swell in the acidic medium. Likewise basic aqueous spills can be best cleaned by a porous material comprising a lightly crosslinked poly(acrylic acid). In addition, amphiphilic aqueous spills can be best cleaned by a porous material comprising a lightly crosslinked poly(ethyleneglycol), which readily absorbs both water and some organic solvents such as, e.g., dioxane and dichloromethane. Lastly, hydrophobic spills can be cleaned using polymers that readily swell in and absorb hydrophobic materials, yet are not dissolved by them.

The present specification discloses, in part, a porous material comprising a matrix defining an array of interconnected pores useful as filtration materials for air and/or liquid filtration. Such porous filtration materials have Porosities for filters may vary from about 80% to approximately 99.9% and average pore size can vary from about 1 um to about 2000 µm. The porous material must be predominantly open celled and with interconnection diameters varying from about 1 µm to about 1800 µm. Such porous filtration materials are typically designed for particular applications by optimizing the affinity of the polymer and porosity of the matrix for the material to be filtration. For example, hydrophilic filtration materials, such as, e.g., filtration materials comprising a matrix composed of fluoropolymer thermosets or poly(vinyl)-based thermoplastics, are readily wetted with aqueous solutions. Hydrophobic filters materials, such as, e.g., filtration materials comprising a matrix composed of cellulose-based thermoplastics or poly (vinyl)-based thermoplastics, are readily wet in low surface-tension liquids, such as organic solvents and silicone oil and are best suited for gas filtration and venting applications. In venting applications, air can pass through these filters without allowing the passage of water. Other filtration applications include the filtering of low surface tension and high surface tension solutions, as well as separation of low surface tension from high surface tension mediums.

The present specification discloses, in part, a porous material comprising a matrix defining an array of interconnected pores useful as filtration materials in a chemically aggressive environment. Such porous filtration materials have porosities for filters may vary from about 80% to approximately 99.9% and average pore size can vary from about 300 µm to about 5000 µm. The porous material must be predominantly open celled and with interconnection diameters varying from about 300 µm to about 5,000 µm. Such porous filtration materials are typically designed for particular applications by optimizing the affinity of the polymer and porosity of the matrix for the material to be filtration. For example, such filtration materials comprising a matrix composed of fluoropolymer thermosets.

The present specification discloses, in part, a porous material comprising a matrix defining an array of interconnected pores having thermally stability. Such a porous material is useful in light weight armor materials like a component of a flack jacket, bullet-proof vest, or armor panels for a vehicle. A porous filtration material suitable as a light weight armor material typically comprises low carbon content materials or other non-combustible materials, such as, e.g., silicone-based elastomers, fluorosilicone-based elastomers, and/or fluoropolymer thermosets. The addition of certain ceramic nanopowders can help retard the projectile or shrapnel with aid of high density high yield strength particulate.

The present specification discloses, in part, a porous material comprising a substantially non-degradable, biocompatible matrix defining an array of interconnected pores. Such a porous material is useful in biomedical materials like a component of a medical device, scaffolds (templates) for tissue engineering/regeneration, wound dressings, drug release matrixes, membranes for separations and filtration, sterile filters, artificial kidneys, absorbents, hemostatic devices, where biocompatibility and resistance to biodegradation are important. For example, the disclosed porous material comprising a substantially non-degradable, biocompatible, matrix has high porosity and interconnected pore structures that favor biomedical applications desiring tissue growth into the porous material, such as, e.g., by facilitating cell migration, cell proliferation, cell differentiation, nutrient exchange, and/or waste removal.

A porous material disclosed herein can be implanted into the soft tissue of an animal. Such a porous material may be completely implanted into the soft tissue of an animal body (i.e., the entire material is within the body), or the device may be partially implanted into an animal body (i.e., only part of the material is implanted within an animal body, the remainder of the material being located outside of the animal body). A porous material disclosed herein can also be affixed to one or more soft tissues of an animal, typically to the skin of an animal body. For example, a strip of porous material can be placed subcutaneously underneath a healing wound or incision to prevent the fibrous tissue from aligning and thereby reducing or preventing scar formation.

As used herein, the term "non-degradable" refers to a material that is not prone to degrading, decomposing, or breaking down to any substantial or significant degree while implanted in the host. Non-limiting examples of substantial non-degradation include less than 10% degradation of a porous material over a time period measured, less than 5% degradation of a porous material over a time period measured, less than 3% degradation of a porous material over a time period measured, less than 1% degradation of a porous material over a time period measured. As used herein, the term "biocompatible" refers to a material's ability to perform its intended function, with a desired degree of incorporation in the host, without eliciting any undesirable local or systemic effects in that host.

In an embodiment, a porous material comprising a matrix defining an array of interconnected pores may, or may not be, substantially non-degradable. In aspects of this embodiment, a porous material disclosed herein is substantially non-degradable for, e.g., about five years, about ten years, about 15 years, about 20 years, about 25 years, about 30 years, about 35 years, about 40 years, about 45 years, or about 50 years. In other aspects of this embodiment, a porous material disclosed herein is substantially non-degradable for, e.g., at least five years, at least ten years, at least 15 years, at least 20 years, at least 25 years, at least 30 years, at least 35 years, at least 40 years, at least 45 years, or at least 50 years. In yet other aspects of this embodiment, a porous material disclosed herein exhibits less than 5% degradation, less than 3% degradation, or less than 1% degradation over for, e.g., about five years, about ten years, about 15 years, about 20 years, about 25 years, about 30 years, about 35 years, about 40 years, about 45 years, or about 50 years. In still other aspects of this embodiment, a porous material disclosed herein exhibits less than 5% degradation, less than 3% degradation, or less than 1% degradation over for, e.g., at least five years, at least ten years, at least 15 years, at least 20 years, at least 25 years, at least 30 years, at least 35 years, at least 40 years, at least 45 years, or at least 50 years.

In another embodiment, a porous material comprising a matrix defining an array of interconnected pores may, or may not be, substantially biocompatible. In aspects of this embodiment, a porous material disclosed herein is substantially biocompatible for, e.g., at least five years, at least ten years, at least 15 years, at least 20 years, at least 25 years, at least 30 years, at least 35 years, at least 40 years, at least 45 years, or at least 50 years.

The present specification discloses in part, methods of making a porous material disclosed herein. The porous materials disclosed herein can be formed as a separate component or can be integrated into a base material.

In one aspect, a method of making a porous material comprises the steps of: a) coating porogens with a matrix material base to form a matrix material-coated porogen mixture; b) treating the matrix material-coated porogen mixture to allow fusing of the porogens to form a porogen scaffold and curing or hardening of the matrix; c) removing the porogen scaffold, wherein porogen scaffold removal results in a porous material, the porous material comprising a matrix defining an array of interconnected pores.

In another aspect, a method of making a porous material comprises the steps of a) coating porogens with a matrix material base to form a matrix material-coated porogen mixture; b) packing porogens into a mold; c) treating the matrix material-coated porogen mixture to allow fusing of the porogens to form a porogen scaffold and curing or hardening of the matrix material; d) removing the porogen scaffold, wherein porogen scaffold removal results in a porous material, the porous material comprising a matrix defining an array of interconnected pores.

As used herein, the term "matrix material base" is synonymous with "matrix base", "material base", "uncured matrix material", "uncured matrix" and "uncured material" and refers to a material disclosed herein, such as, e.g., a thermoset polymer, an elastomer, or a thermoplastic elastomer, that is in its uncured state; or a material disclosed herein, such as, e.g., a thermoplastic polymer, that is in its fluid or soft state.

As used herein, the term "porogen" refers to any structure that can be used to create a porogen scaffold that is removable after a matrix is formed under conditions that do not destroy the matrix. Porogens can be made of any material having a glass transition temperature ($T_g$) or melting temperature ($T_m$) from about 30° C. to about 100° C. In addition, porogens useful to practice aspects of the present specification should be soluble in hydrophilic solvents such as, e.g., water, dimethyl sulfoxide (DMSO), methylene chloride, chloroform, and acetone. However, porogens useful to practice aspects of the present specification should not be soluble in aromatic solvents like xylene, chlorinated solvents like dichloromethane, or any other solvent used to disperse uncured matrix material base. Exemplary porogens suitable for use in the methods disclosed herein, include, without limitation, salts, such as, e.g., sodium chloride, potassium chloride, sodium fluoride, potassium fluoride, sodium iodide, sodium nitrate, sodium sulfate, sodium iodate, and/or mixtures thereof; sugars and/or its derivatives, such as, e.g., glucose, fructose, sucrose, lactose, maltose, saccharin, and/or mixtures thereof; polysaccharides and their derivatives, such as, e.g., cellulose and hydroxyethylcellulose; waxes, such as, e.g., paraffin, beeswax, and/or mixtures thereof; other water soluble chemicals, such as, e.g., sodium hydroxide; naphthalene; polymers, such as, e.g., poly(alkylene oxide), poly (acrylamide), poly(acrylic acid), poly(acrylamide-co-arylic acid), poly(acrylamide-co-diallyldimethylammonium chloride), polyacrylonitrile, poly(allylamine), poly(amide), poly (anhydride), poly(butylene), poly($\epsilon$-caprolactone), poly(carbonate), poly(ester), poly(etheretherketone), poly (ethersulphone), poly(ethylene), poly(ethylene alcohol), poly (ethylenimine), poly(ethylene glycol), poly(ethylene oxide), poly(glycolide) ((like poly(glycolic acid)), poly(hydroxy butyrate), poly(hydroxyethylmethacrylate), poly(hydroxypropylmethacrylate), poly(hydroxystyrene), poly(imide), poly(lactide) poly(L-lactic acid) and poly(D,L-lactic acid)), poly(lactide-co-glycolide), poly(lysine), poly(methacrylate), poly(methylmethacrylate), poly(orthoester), poly(phenylene oxide), poly(phosphazene), poly(phosphoester), poly(propylene fumarate), poly(propylene), poly(propylene glycol), poly(propylene oxide), poly(styrene), poly(sulfone), poly (tetrafluoroethylene), poly(vinylacetate), poly(vinyl alcohol), poly(vinylchloride), poly(vinylidene fluoride), poly(vinyl pyrrolidone), poly(urethane), any copolymer thereof (like poly(ethylene oxide)), poly(propylene oxide), copolymers (poloxamers), poly(vinyl alcohol-co-ethylene), poly(styrene-co-allyl) alcohol, and poly(ethylene)-block-poly(ethylene glycol), and/or any mixtures thereof; as well as alginate, chitin, chitosan, collagen, dextran, gelatin, hyaluronic acid, pectin, and/or mixtures thereof. Methods for making porogens are well known in the art and non-limiting examples of such methods are described in, e.g., Peter X. Ma, Reverse Fabrication of Porous Materials, US 2002/00056000; P. X. Ma and G. Wei, Particle-Containing Complex Porous Materials, U.S. 2006/0246121; and F. Liu, et al., *Porogen Compositions, Methods of Making and Uses*; each of which is hereby incorporated by reference in its entirety. Porogens are also commercially available from, e.g., Polyscience Inc. (Warrington, Pa.).

Porogens have a shape sufficient to allow formation of a porogen scaffold useful in making a matrix as disclosed herein. Any porogen shape is useful with the proviso that the porogen shape is sufficient to allow formation of a porogen scaffold useful in making a matrix as disclosed herein. Useful porogen shapes include, without limitation, roughly spherical, perfectly spherical, ellipsoidal, polyhedronal, triangular, pyramidal, quadrilateral like squares, rectangles, parallelograms, trapezoids, rhombus and kites, and other types of polygonal shapes.

In an embodiment, porogens have a shape sufficient to allow formation of a porogen scaffold useful in making a matrix as disclosed herein. In aspects of this embodiment, porogens have a shape that is roughly spherical, perfectly spherical, ellipsoidal, polyhedronal, triangular, pyramidal, quadrilateral, or polygonal.

Porogens have a roundness sufficient to allow formation of a porogen scaffold useful in making a matrix as disclosed herein. As used herein, "roundness" is defined as $(6 \times V)/(\pi \times D^3)$, where V is the volume and D is the diameter. Any porogen roundness is useful with the proviso that the porogen roundness is sufficient to allow formation of a porogen scaffold useful in making a matrix as disclosed herein.

In an embodiment, porogens has a roundness sufficient to allow formation of a porogen scaffold useful in making a matrix as disclosed herein. In aspects of this embodiment, porogens have a mean roundness of, e.g., about 0.1, about 0.2, about 0.3, about 0.4, about 0.5, about 0.6, about 0.7, about 0.8, about 0.9, or about 1.0. In other aspects of this embodiment, porogens have a mean roundness of, e.g., at least 0.1, at least 0.2, at least 0.3, at least 0.4, at least 0.5, at least 0.6, at least 0.7, at least 0.8, at least 0.9, or at least 1.0. In yet other aspects of this embodiment, porogens have a mean roundness of, e.g., at most 0.1, at most 0.2, at most 0.3, at most 0.4, at most 0.5, at most 0.6, at most 0.7, at most 0.8, at most 0.9, or at most 1.0. In still other aspects of this embodiment, porogens have a mean roundness of, e.g., about 0.1 to about 1.0, about 0.2 to about 1.0, about 0.3 to about 1.0, about 0.4 to about 1.0, about 0.5 to about 1.0, about 0.6 to about 1.0, about 0.7 to about 1.0, about 0.8 to about 1.0, about 0.9 to about 1.0, about 0.1 to about 0.9, about 0.2 to about 0.9, about 0.3 to about 0.9, about 0.4 to about 0.9, about 0.5 to about 0.9, about 0.6 to about 0.9, about 0.7 to about 0.9, about 0.8 to about 0.9, about 0.1 to about 0.8, about 0.2 to about 0.8, about 0.3 to about 0.8, about 0.4 to about 0.8, about 0.5 to about 0.8, about 0.6 to about 0.8, about 0.7 to about 0.8, about 0.1 to about 0.7, about 0.2 to about 0.7, about 0.3 to about 0.7, about 0.4 to about 0.7, about 0.5 to about 0.7, about 0.6 to about 0.7, about 0.1 to about 0.6, about 0.2 to about 0.6, about 0.3 to about 0.6, about 0.4 to about 0.6, about 0.5 to about 0.6, about 0.1 to about 0.5, about 0.2 to about 0.5, about 0.3 to about 0.5, or about 0.4 to about 0.5.

The present specification discloses, in part, coating a matrix material base with porogens to form a matrix material-coated porogen mixture. Suitable matrix material bases are as described above. Coating the porogens with a matrix material base can be accomplished by any suitable means, including, without limitation, mechanical application such as, e.g., dipping, spraying, knifing, curtaining, brushing, or vapor deposition, thermal application, adhering application, chemical bonding, self-assembling, molecular entrapment, and/or any combination thereof. The matrix material base is applied to the porogens in such a manner as to coat the porogens with the desired thickness of the matrix material. Removal of excess matrix material can be accomplished by any suitable means, including, without limitation, gravity-based filtering or sieving, vacuum-based filtering or sieving, blowing, and/or any combination thereof.

Thus, in an embodiment, porogens are coated with a matrix material base to a thickness sufficient to enable the desired function of the porous material. In aspects of this embodiment, porogens are coated with a matrix material base to a thickness of, e.g., about 1 µm, about 2 µm, about 3 µm, about 4 µm, about 5 µm, about 6 µm, about 7 µm, about 8 µm, about 9 µm, about 10 µm, about 20 µm, about 30 µm, about 40 µm, about 50 µm, about 60 µm, about 70 µm, about 80 µm, about 90 µm, or about 100 µm. In other aspects of this embodiment, porogens are coated with a matrix material base to a thickness of, e.g., at least 1 µm, at least 2 µm, at least 3 µm, at least 4 µm, at least 5 µm, at least 6 µm, at least 7 µm, at least 8 µm, at least 9 µm, at least 10 µm, at least 20 µm, at least 30 µm, at least 40 µm, at least 50 µm, at least 60 µm, at least 70 µm, at least 80 µm, at least 90 µm, or at least 100 µm. In yet other aspects of this embodiment, porogens are coated with a matrix material base to a thickness of, e.g., at most 1 µm, at most 2 µm, at most 3 µm, at most 4 µm, at most 5 µm, at most 6 µm, at most 7 µm, at most 8 µm, at most 9 µm, at most 10 µm, at most 20 µm, at most 30 µm, at most 40 µm, at most 50 µm, at most 60 µm, at most 70 µm, at most 80 µm, at most 90 µm, or at most 100 µm. In still other aspects of this embodiment, porogens are coated with a matrix material base to a thickness of, e.g., about 1 µm to about 5 µm, about 1 µm to about 10 µm, about 5 µm to about 10 µm, about 5 µm to about 25 µm, about 5 µm to about 50 µm, about 10 µm to about 50 µm, about 10 µm to about 75 µm, about 10 µm to about 100 µm, about 25 µm to about 100 µm, or about 50 µm to about 100 µm.

The present specification discloses, in part, devolitalizing a matrix material-coated porogens. As used herein, the term "devolitalizing" or "devolitalization" refers to a process that removes volatile components from the matrix material-coated porogens. Devolitalization of the matrix material-coated porogens can be accomplished by any suitable means that removes substantially all the volatile components from the matrix material-coated porogens. Non-limiting examples of devolitalizing procedures include evaporation, freeze-drying, sublimation, extraction, and/or any combination thereof.

In an embodiment, a matrix material-coated porogens is devolitalized at a single temperature for a time sufficient to allow the evaporation of substantially all volatile components from the matrix material-coated porogens. In an aspect of this embodiment, a matrix material-coated porogens are devolitalized at ambient temperature for about 1 minute to about 5 minutes. In another aspect of this embodiment, a matrix material-coated porogens are devolitalized at ambient temperature for about 45 minutes to about 75 minutes. In yet another aspect of this embodiment, a matrix material-coated porogens are devolitalized at ambient temperature for about 90 minutes to about 150 minutes. In another aspect of this embodiment, a matrix material-coated porogens are devolitalized at about 18° C. to about 22° C. for about 1 minute to about 5 minutes. In yet another aspect of this embodiment, a matrix material-coated porogens are devolitalized at about 18° C. to about 22° C. for about 45 minutes to about 75 minutes. In still another aspect of this embodiment, a matrix material-coated porogens are devolitalized at about 18° C. to about 22° C. for about 90 minutes to about 150 minutes.

The present specification discloses, in part, packing porogens into a mold prior to fusion. Any mold shape may be used for packing the porogens. As a non-limiting example, a mold shape can be a shell that outlines the contours an implantable device, such as, e.g., a shell for a breast implant, or a shell for a muscle implant. As another non-limiting example, the mold shape can be one that forms sheets. Such sheets can be made in a wide variety or proportions based on the needed application. For example, the sheets can be made in a size slightly bigger that an implantable medical device so that there is sufficient material to cover the device and allow for trimming of the excess. As another example, the sheets can be produced as a continuous roll that allows a person skilled in the art to take only the desired amount for an application, such as, e.g., creating strips having a textured surface for control of scar formation. As yet another non-limiting example, a mold shape can be a three-dimensional form that represents the final shape of the porous material, such as, e.g., a filter, an insulating material, a light armor panel. The porogens may be packed into a mold using ultrasonic agitation, mechanical agitation, or any other suitable method for obtaining a closely packed array of porogens.

In an embodiment, a matrix material-coated porogen mixture is packed into a mold. In an aspect of this embodiment, a matrix material-coated porogen mixture is packed into a mold in a manner suitable obtaining a closely packed array of porogens. In other aspects of this embodiment, a matrix material-coated porogen mixture is packed into a mold using sonic agitation or mechanical agitation.

The present specification discloses, in part, treating a matrix material-coated porogen mixture to allow fusing of the porogens to form a porogen scaffold and curing or hardening of the matrix material base. As used herein, the term "treating" refers to a process that 1) fuses the porogens to form a porogen scaffold useful to make a matrix as disclosed herein and 2) cures the matrix material base (e.g., a thermoset, an elastomer, a thermoplastic elastomer) to form a matrix comprising an array of interconnected of pores as disclosed herein; or hardens the matrix material base (e.g., a thermoplastic) to form a matrix comprising an array of interconnected of pores as disclosed herein. As used herein, the term "curing" is synonymous with "setting" or "vulcanizing" and refers to an irreversible process that exposes the chains of a polymer to a element which activates a phase change in the polymer to a more stable state, such as, e.g., by physically or chemically cross-linked polymer chains to one another. As used herein, the term "hardening" refers to a reversible process where the matrix material transitions from a fluid state to a solid state, as typified for a thermoplastic. Non-limiting examples of treating include thermal treating, chemical treating, catalyst treating, radiation treating, and physical treating. Treating of a matrix material-coated porogen scaffold can be done under any condition for any length of time with the proviso that the treating fuses the porogens to form a porogen scaffold useful to make a matrix as disclosed herein and cures or hardens the matrix material.

Thermal treating a matrix material-coated porogen mixture can be at any temperature or temperatures for any length of time or times with the proviso that the thermal treatment fuses the porogens to form a porogen scaffold and cures or hardens the matrix material base. A non-limiting example of temperatures useful in a thermal treatment are temperatures higher than the glass transition temperature or melting temperature of the porogens, such as between about 5° C. to about 50° C. higher than the glass transition temperature or melting temperature of the porogens. Any temperature can be used in a thermal treatment with the proviso that the temperature is sufficient to cause fusion of the porogens. As a non-limiting example, the thermal treatment can be from about 30° C. to about 250° C. Increasing the duration of the thermal treatment at a given temperature increases the connection size; increases the sintering temperature, and increases the growth rate of the connections. Any time can be used in a thermal treatment with the proviso that the time is sufficient to cause fusion of the porogens and cures or hardens the matrix material base. Suitable times are generally from about 0.5 hours to about 48 hours.

Thus, in an embodiment, matrix material-coated porogens are treated by thermal treatment, chemical treatment, catalyst treatment, radiation treatment, or physical treatment. In another embodiment, matrix material-coated porogens are treated at a single time, where the curing time is sufficient to form a matrix comprising an array of interconnected of pores as disclosed herein.

In another embodiment, matrix material-coated porogens are thermal treated at a single temperature for a single time, where the treating temperature and time is sufficient to fuse the porogens to form a porogen scaffold and cure or harden the matrix material base.

In other aspects of this embodiment, a thermal treatment comprises heating a matrix material-coated porogens for a time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperature and time is sufficient to fuse the porogens to form a porogen scaffold and cure or harden the matrix material base. In yet other aspects of this embodiment, a thermal treatment comprises heating a matrix material-coated porogens for a time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperature and time is sufficient to fuse the porogens to form a porogen scaffold and cure or harden the matrix material base. In still other aspects of this embodiment, a thermal treatment comprises heating a matrix material-coated porogens for a time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperature and time is sufficient to fuse the porogens to form a porogen scaffold and cure or harden the matrix material base. In further aspects of this embodiment, a thermal treatment comprises heating a matrix material-coated porogens for a time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperature and time is sufficient to fuse the porogens to form a porogen scaffold and cure or harden the matrix material base.

In another aspect of this embodiment, the thermal treatment comprises heating a matrix material-coated porogen scaffold is treated at about 30° C. to about 130° C. for about 10 minutes to about 360 minutes, where the treating temperature and time is sufficient to fuse the porogens to form a porogen scaffold and cure or harden the matrix material base.

In yet another embodiment, a matrix material-coated porogens are thermal treated at a plurality of temperatures for a plurality of times, where the treating temperatures and times are sufficient to fuse the porogens to form a porogen scaffold and cure or harden the matrix material base. In an aspect of this embodiment, matrix material-coated porogens are treated at a first temperature for a first time, and then a second temperature for a second time, where the treating temperatures and times are sufficient to fuse the porogens to form a porogen scaffold and cure or harden the matrix material base, and where the first and second temperatures are different.

In aspects of this embodiment, thermal treatment comprises heating the matrix material-coated porogens at a first temperature for a first time, and then heating the porogens at a second temperature for a second time, where the treating temperatures and times are sufficient to fuse the porogens to form a porogen scaffold and cure or harden the matrix material base, and where the first and second temperatures are different, different, In other aspects of this embodiment, a thermal treatment comprises heating a matrix material-coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the matrix material-coated porogens, then heating for a second time the porogens at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and cure or harden the matrix material base, and where the first and second temperatures are different. In yet other aspects of this embodiment, a thermal treatment comprises heating a matrix material-coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating the matrix material-coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and cure or harden the matrix material base, and where the first and second temperatures are different. In still other aspects of this embodiment, a thermal treatment comprises heating a matrix material-coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating the matrix material-coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and cure or harden the matrix material base, and where the first and second temperatures are different.

In further aspects of this embodiment, a thermal treatment comprises heating a matrix material-coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating the matrix material-coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and cure or harden the matrix material base, and where the first and second temperatures are different.

In other aspects of this embodiment, thermal treatment comprises heating the matrix material-coated porogens at a first temperature for a first time, heating the porogens at a second temperature for a second time, and then heating the porogens at a third temperature at a third time, where the treating temperatures and times are sufficient to fuse the porogens to form a porogen scaffold and cure or harden the matrix material base, and where the first temperature is different from the second temperature and the second temperature is different from the third temperature.

In other aspects of this embodiment, a thermal treatment comprises heating a matrix material-coated porogens for a first time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating the matrix material-coated porogens for a second time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, then heating the matrix material-coated porogens for a third time at, e.g., about 5° C. higher, about 10° C. higher, about 15° C. higher, about 20° C. higher, about 25° C. higher, about 30° C. higher, about 35° C. higher, about 40° C. higher, about 45° C. higher, or about 50° C. higher than the melting temperature or glass transition temperature of the porogens, where the treating temperatures and times are sufficient to fuse the porogens to form a porogen scaffold and cure or harden the matrix material base, and where the first temperature is different from the second temperature and the second temperature is different from the third temperature. In yet other aspects of this embodiment, a thermal treatment comprises heating a matrix material-coated porogens for a first time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating the matrix material-coated porogens for a second time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, then heating the matrix material-coated porogens for a third time at, e.g., at least 5° C. higher, at least 10° C. higher, at least 15° C. higher, at least 20° C. higher, at least 25° C. higher, at least 30° C. higher, at least 35° C. higher, at least 40° C. higher, at least 45° C. higher, or at least 50° C. higher than the melting temperature or glass transition temperature of the porogens, where the treating temperatures and times are sufficient to fuse the porogens to form a porogen scaffold and cure or harden the matrix material base, and where the first temperature is different from the second temperature and the second temperature is different from the third temperature. In still other aspects of this embodiment, a thermal treatment comprises heating a matrix material-coated porogens for a first time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating the matrix material-coated porogens for a second time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, then heating the matrix material-coated porogens for a third time at, e.g., at most 5° C. higher, at most 10° C. higher, at most 15° C. higher, at most 20° C. higher, at most 25° C. higher, at most 30° C. higher, at most 35° C. higher, at most 40° C. higher, at most 45° C. higher, or at most 50° C. higher than the melting temperature or glass transition temperature of the porogens, where the treating temperatures and times are sufficient to fuse the porogens to form a porogen scaffold and cure or harden the matrix material base, and where the first temperature is different from the second temperature and the second temperature is different from the third temperature.

In further aspects of this embodiment, a thermal treatment comprises heating a matrix material-coated porogens for a first time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating the matrix material-coated porogens for a second time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, then heating the matrix material-coated porogens for a third time at, e.g., about 5° C. higher to about 10° C. higher, about 5° C. higher to about 15° C. higher, about 5° C. higher to about 20° C. higher, about 5° C. higher to about 25° C. higher, about 5° C. higher to about 30° C. higher, about 5° C. higher to about 35° C. higher, about 5° C. higher to about 40° C. higher, about 5° C. higher to about 45° C. higher, about 5° C. higher to about 50° C. higher, about 10° C. higher to about 15° C. higher, about 10° C. higher to about 20° C. higher, about 10° C. higher to about 25° C. higher, about 10° C. higher to about 30° C. higher, about 10° C. higher to about 35° C. higher, about 10° C. higher to about 40° C. higher, about 10° C. higher to about 45° C. higher, or about 10° C. higher to about 50° C. higher than the melting temperature or glass transition temperature of the porogens, where the treating temperatures and times are sufficient to fuse the porogens to form a porogen scaffold and cure or harden the matrix material base, and where the first temperature is different from the second temperature and the second temperature is different from the third temperature.

In still other aspect of this embodiment, matrix material-coated porogens are treated at about 60° C. to about 75° C. for about 15 minutes to about 45 minutes, and then at about 120° C. to about 130° C. for about 60 minutes to about 90 minutes, where the treating temperatures and times is sufficient to fuse the porogens to form a porogen scaffold and cure or harden the matrix material base. In a further aspect of this embodiment, matrix material-coated porogen mixture is treated at about 60° to about 75° C. for about 15 minutes to about 45 minutes, then at about 135° C. to about 150° C. for about 90 minutes to about 150 minutes, and then at about 150° C. to about 165° C. for about 15 minutes to about 45 minutes.

The present specification discloses, in part, to form a porogen scaffold. As used herein, the term "porogen scaffold" refers to a three-dimensional structural framework composed of fused porogens that serves as the negative replica of the matrix defining an interconnected array or pores as disclosed herein.

The porogen scaffold is formed in such a manner that substantially all the fused porogens in the porogen scaffold have a similar diameter. As used herein, the term "substantially", when used to describe fused porogen, refers to at least 90% of the porogen comprising the porogen scaffold are fused, such as, e.g., at least 95% of the porogens are fused or at least 97% of the porogen are fused. As used herein, the term "similar diameter", when used to describe fused porogen, refers to a difference in the diameters of the two fused porogen that is less than about 20% of the larger diameter. As used herein, the term "diameter", when used to describe fused porogen, refers to the longest line segment that can be drawn that connects two points within the fused porogen, regardless of whether the line passes outside the boundary of the fused porogen. Any fused porogen diameter is useful with the proviso that the fused porogen diameter is sufficient to allow formation of a porogen scaffold useful in making a matrix as disclosed herein.

The porogen scaffold is formed in such a manner that the diameter of the connections between each fused porogen is sufficient to allow formation of a porogen scaffold useful in making a matrix as disclosed herein. As used herein, the term "diameter", when describing the connection between fused porogens, refers to the diameter of the cross-section of the connection between two fused porogens in the plane normal to the line connecting the centroids of the two fused porogens, where the plane is chosen so that the area of the cross-section of the connection is at its minimum value. As used herein, the term "diameter of a cross-section of a connection" refers to the average length of a straight-line segment that passes through the center, or centroid (in the case of a connection having a cross-section that lacks a center), of the cross-section of a connection and terminates at the periphery of the cross-section. As used herein, the term "substantially", when used to describe the connections between fused porogens refers to at least 90% of the fused porogens comprising the porogen scaffold make connections between each other, such as, e.g., at least 95% of the fused porogens make connections between each other or at least 97% of the fused porogens make connections between each other.

In an embodiment, a porogen scaffold comprises fused porogens where substantially all the fused porogens have a similar diameter. In aspects of this embodiment, at least 90% of all the fused porogens have a similar diameter, at least 95% of all the fused porogens have a similar diameter, or at least 97% of all the fused porogens have a similar diameter. In another aspect of this embodiment, difference in the diameters of two fused porogens is, e.g., less than about 20% of the larger diameter, less than about 15% of the larger diameter, less than about 10% of the larger diameter, or less than about 5% of the larger diameter.

In another embodiment, a porogen scaffold comprises fused porogens have a mean diameter sufficient to enable the desired function of the porous material. In aspects of this embodiment, a porogen scaffold comprises fused porogens comprising mean fused porogen diameter of, e.g., about 50 µm, about 75 µm, about 100 µm, about 150 µm, about 200 µm, about 250 µm, about 300 µm, about 350 µm, about 400 µm, about 450 µm, or about 500 µm. In other aspects, a porogen scaffold comprises fused porogens comprising mean fused porogen diameter of, e.g., about 500 µm, about 600 µm, about 700 µm, about 800 µm, about 900 µm, about 1000 µm, about 1500 µm, about 2000 µm, about 2500 µm, or about 3000 µm. In yet other aspects of this embodiment, a porogen scaffold comprises fused porogens comprising mean fused porogen diameter of, e.g., at least 50 µm, at least 75 µm, at least 100 µm, at least 150 µm, at least 200 µm, at least 250 µm, at least 300 µm, at least 350 µm, at least 400 µm, at least 450 µm, or at least 500 µm. In still other aspects, a matrix comprises fused porogens comprising mean fused porogen diameter of, e.g., at least 500 µm, at least 600 µm, at least 700 µm, at least 800 µm, at least 900 µm, at least 1000 µm, at least 1500 µm, at least 2000 µm, at least 2500 µm, or at least 3000 µm. In further aspects of this embodiment, a porogen scaffold comprises fused porogens comprising mean fused porogen diameter of, e.g., at most 50 µm, at most 75 µm, at most 100 µm, at most 150 µm, at most 200 µm, at most 250 µm, at most 300 µm, at most 350 µm, at most 400 µm, at most 450 µm, or at most 500 µm. In yet further aspects of this embodiment, a matrix comprises fused porogens comprising mean fused porogen diameter of, e.g., at most 500 µm, at most 600 µm, at most 700 µm, at most 800 µm, at most 900 µm, at most 1000 µm, at most 1500 µm, at most 2000 µm, at most 2500 µm, or at most 3000 µm. In still further aspects of this embodiment, a porogen scaffold comprises fused porogens comprising mean fused porogen diameter in a range from, e.g., about 300 µm to about 600 µm, about 200 µm to about 700 µm, about 100 µm to about 800 µm, about 500 µm to about 800 µm, about 50 µm to about 500 µm, about 75 µm to about 500 µm, about 100 µm to about 500 µm, about 200 µm to about 500 µm, about 300 µm to about 500 µm, about 50 µm to about 1000 µm, about 75 µm to about 1000 µm, about 100 µm to about 1000 µm, about 200 µm to about 1000 µm, about 300 µm to about 1000 µm, about 50 µm to about 1000 µm, about 75 µm to about 3000 µm, about 100 µm to about 3000 µm, about 200 µm to about 3000 µm, or about 300 µm to about 3000 µm.

In another embodiment, a porogen scaffold comprises fused porogens connected to a plurality of other porogens. In aspects of this embodiment, a porogen scaffold comprises a mean fused porogen connectivity, e.g., about two other fused porogens, about three other fused porogens, about four other fused porogens, about five other fused porogens, about six other fused porogens, about seven other fused porogens, about eight other fused porogens, about nine other fused porogens, about ten other fused porogens, about 11 other fused porogens, or about 12 other fused porogens. In other aspects of this embodiment, a porogen scaffold comprises a mean fused porogen connectivity, e.g., at least two other fused porogens, at least three other fused porogens, at least four other fused porogens, at least five other fused porogens, at least six other fused porogens, at least seven other fused porogens, at least eight other fused porogens, at least nine other fused porogens, at least ten other fused porogens, at least 11 other fused porogens, or at least 12 other fused porogens. In yet other aspects of this embodiment, a porogen scaffold comprises a mean fused porogen connectivity, e.g., at most two other fused porogens, at most three other fused porogens, at most four other fused porogens, at most five other fused porogens, at most six other fused porogens, at most seven other fused porogens, at most eight other fused porogens, at most nine other fused porogens, at most ten other fused porogens, at most 11 other fused porogens, or at most 12 other fused porogens.

In still other aspects of this embodiment, a porogen scaffold comprises fused porogens connected to, e.g., about two other fused porogens to about 12 other fused porogens, about two other fused porogens to about 11 other fused porogens, about two other fused porogens to about ten other fused porogens, about two other fused porogens to about nine other fused porogens, about two other fused porogens to about eight other fused porogens, about two other fused porogens to about seven other fused porogens, about two other fused porogens to about six other fused porogens, about two other fused porogens to about five other fused porogens, about three other fused porogens to about 12 other fused porogens, about three other fused porogens to about 11 other fused porogens, about three other fused porogens to about ten other fused porogens, about three other fused porogens to about nine other fused porogens, about three other fused porogens to about eight other fused porogens, about three other fused porogens to about seven other fused porogens, about three other fused porogens to about six other fused porogens, about three other fused porogens to about five other fused porogens, about four other fused porogens to about 12 other fused porogens, about four other fused porogens to about 11 other fused porogens, about four other fused porogens to about ten other fused porogens, about four other fused porogens to about nine other fused porogens, about four other fused porogens to about eight other fused porogens, about four other fused porogens to about seven other fused porogens, about four other fused porogens to about six other fused porogens, about four other fused porogens to about five other fused porogens, about five other fused porogens to about 12 other fused porogens, about five other fused porogens to about 11 other fused porogens, about five other fused porogens to about ten other fused porogens, about five other fused porogens to about nine other fused porogens, about five other fused porogens to about eight other fused porogens, about five other fused porogens to about seven other fused porogens, or about five other fused porogens to about six other fused porogens.

In another embodiment, a porogen scaffold comprises fused porogens where the diameter of the connections between the fused porogens is sufficient to enable the desired function of the porous material. In aspects of this embodiment, the porogen scaffold comprises fused porogens where the diameter of the connections between the fused porogens is, e.g., about 10% the mean fused porogen diameter, about 20% the mean fused porogen diameter, about 30% the mean fused porogen diameter, about 40% the mean fused porogen diameter, about 50% the mean fused porogen diameter, about 60% the mean fused porogen diameter, about 70% the mean fused porogen diameter, about 80% the mean fused porogen diameter, or about 90% the mean fused porogen diameter. In other aspects of this embodiment, the porogen scaffold comprises fused porogens where the diameter of the connections between the fused porogens is, e.g., at least 10% the mean fused porogen diameter, at least 20% the mean fused porogen diameter, at least 30% the mean fused porogen diameter, at least 40% the mean fused porogen diameter, at least 50% the mean fused porogen diameter, at least 60% the mean fused porogen diameter, at least 70% the mean fused porogen diameter, at least 80% the mean fused porogen diameter, or at least 90% the mean fused porogen diameter. In yet other aspects of this embodiment, the porogen scaffold comprises fused porogens where the diameter of the connections between the fused porogens is, e.g., at most 10% the mean fused porogen diameter, at most 20% the mean fused porogen diameter, at most 30% the mean fused porogen diameter, at most 40% the mean fused porogen diameter, at most 50% the mean fused porogen diameter, at most 60% the mean fused porogen diameter, at most 70% the mean fused porogen diameter, at most 80% the mean fused porogen diameter, or at most 90% the mean fused porogen diameter.

In still other aspects of this embodiment, a porogen scaffold comprises fused porogens where the diameter of the connections between the fused porogens is, e.g., about 10% to about 90% the mean fused porogen diameter, about 15% to about 90% the mean fused porogen diameter, about 20% to about 90% the mean fused porogen diameter, about 25% to about 90% the mean fused porogen diameter, about 30% to about 90% the mean fused porogen diameter, about 35% to about 90% the mean fused porogen diameter, about 40% to about 90% the mean fused porogen diameter, about 10% to about 80% the mean fused porogen diameter, about 15% to about 80% the mean fused porogen diameter, about 20% to about 80% the mean fused porogen diameter, about 25% to about 80% the mean fused porogen diameter, about 30% to about 80% the mean fused porogen diameter, about 35% to about 80% the mean fused porogen diameter, about 40% to about 80% the mean fused porogen diameter, about 10% to about 70% the mean fused porogen diameter, about 15% to about 70% the mean fused porogen diameter, about 20% to about 70% the mean fused porogen diameter, about 25% to about 70% the mean fused porogen diameter, about 30% to about 70% the mean fused porogen diameter, about 35% to about 70% the mean fused porogen diameter, about 40% to about 70% the mean fused porogen diameter, about 10% to about 60% the mean fused porogen diameter, about 15% to about 60% the mean fused porogen diameter, about 20% to about 60% the mean fused porogen diameter, about 25% to about 60% the mean fused porogen diameter, about 30% to about 60% the mean fused porogen diameter, about 35% to about 60% the mean fused porogen diameter, about 40% to about 60% the mean fused porogen diameter, about 10% to about 50% the mean fused porogen diameter, about 15% to about 50% the mean fused porogen diameter, about 20% to about 50% the mean fused porogen diameter, about 25% to about 50% the mean fused porogen diameter, about 30% to about 50% the mean fused porogen diameter, about 10% to about 40% the mean fused porogen diameter, about 15% to about 40% the mean fused porogen diameter, about 20% to about 40% the mean fused porogen diameter, about 25% to about 40% the mean fused porogen diameter, or about 30% to about 40% the mean fused porogen diameter.

The present specification discloses, in part, removing a porogen scaffold from a cured or hardened matrix material. Removal of the porogen scaffold can be accomplished by any suitable means, with the proviso that the resulting porous material comprises a matrix defining an array of interconnected pores useful for its intended purpose. Non-limiting examples of porogen removal include solvent extraction, thermal decomposition extraction, degradation extraction, mechanical extraction, and/or any combination thereof. The resulting porous material comprising a matrix defining an array of interconnected pores is as described herein. In extraction methods requiring exposure to another solution, such as, e.g., solvent extraction, the extraction can incorporate a plurality of solution changes over time to facilitate removal of the porogen scaffold. Non-limiting examples of solvents useful for solvent extraction include water, methylene chloride, acetic acid, formic acid, pyridine, tetrahydrofuran, dimethylsulfoxide, dioxane, benzene, and/or mixtures thereof. A mixed solvent can be in a ratio of higher than about 1:1, first solvent to second solvent or lower than about 1:1, first solvent to second solvent.

in an embodiment, a porogen scaffold is removed by extraction, where the extraction removes substantially all the porogen scaffold leaving a matrix defining an array of interconnected pores. In aspects of this embodiment, a porogen scaffold is removed by extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold, in an aspect, a porogen scaffold is removed by a solvent extraction, a thermal decomposition extraction, a degradation extraction, a mechanical extraction, and/or any combination thereof.

In another embodiment, a porogen scaffold is removed by solvent extraction, where the extraction removes substantially all the porogen scaffold leaving a matrix defining an array of interconnected pores. In aspects of this embodiment, a porogen scaffold is removed by solvent extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by solvent extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by solvent extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In yet another embodiment, a porogen scaffold is removed by thermal decomposition extraction, where the extraction removes substantially all the porogen scaffold leaving a matrix defining an array of interconnected pores. In aspects of this embodiment, a porogen scaffold is removed by thermal extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by thermal extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by thermal extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by degradation extraction, where the extraction removes substantially all the porogen scaffold leaving a matrix defining an array of interconnected pores. In aspects of this embodiment, a porogen scaffold is removed by degradation extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by degradation extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by degradation extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

In still another embodiment, a porogen scaffold is removed by mechanical extraction, where the extraction removes substantially all the porogen scaffold leaving a matrix defining an array of interconnected pores. In aspects of this embodiment, a porogen scaffold is removed by mechanical extraction, where the extraction removes, e.g., about 75% of the porogen scaffold, about 80% of the porogen scaffold, about 85% of the porogen scaffold, about 90% of the porogen scaffold, or about 95% of the porogen scaffold. In other aspects of this embodiment, a porogen scaffold is removed by mechanical extraction, where the extraction removes, e.g., at least 75% of the porogen scaffold, at least 80% of the porogen scaffold, at least 85% of the porogen scaffold, at least 90% of the porogen scaffold, or at least 95% of the porogen scaffold. In aspects of this embodiment, a porogen scaffold is removed by mechanical extraction, where the extraction removes, e.g., about 75% to about 90% of the porogen scaffold, about 75% to about 95% of the porogen scaffold, about 75% to about 100% of the porogen scaffold, about 80% to about 90% of the porogen scaffold, about 80% to about 95% of the porogen scaffold, about 80% to about 100% of the porogen scaffold, about 85% to about 90% of the porogen scaffold, about 85% to about 95% of the porogen scaffold, or about 85% to about 100% of the porogen scaffold.

The present specification discloses in part, biocompatible implantable device comprising a layer of porous material as disclosed herein, wherein the porous material covers a surface of the device. A biocompatible implantable device is synonymous with "medical device", "biomedical device", "implantable medical device" or "implantable biomedical device" and includes, without limitation, pacemakers, dura mater substitutes, implantable cardiac defibrillators, tissue expanders, and tissue implants used for prosthetic, reconstructive, or aesthetic purposes, like breast implants, muscle implants or implants that reduce or prevent scarring. Examples of biocompatible implantable devices that the porous material disclosed herein can be attached to are described in, e.g., Schuessler, Rotational Molding System for Medical Articles, U.S. Pat. No. 7,628,604; Smith, Mastopexy Stabilization Apparatus and Method, U.S. Pat. No. 7,081,135; Knisley, Inflatable Prosthetic Device, U.S. Pat. No. 6,936,068; Falcon, Reinforced Radius Mammary Prostheses and Soft Tissue Expanders, U.S. Pat. No. 6,605,116; Schuessler, Rotational Molding of Medical Articles, U.S. Pat. No. 6,602,452; Murphy, Seamless Breast Prosthesis, U.S. Pat. No. 6,074,421; Knowlton, Segmental Breast Expander For Use in Breast Reconstruction, U.S. Pat. No. 6,071,309; VanBeek, Mechanical Tissue Expander, U.S. Pat. No. 5,882,353; Hunter, Soft Tissue Implants and Anti-Scarring Agents, Schuessler, Self-Sealing Shell For Inflatable Prostheses, U.S. Patent Publication 2010/0049317; U.S. 2009/0214652; Schraga, Medical Implant Containing Detection Enhancing Agent and Method For Detecting Content Leakage, U.S. Patent Publication 2009/0157180; Schuessler, All-Barrier Elastomeric Gel-Filled Breast Prosthesis, U.S. Patent Publication 2009/0030515; Connell, Differential Tissue Expander Implant, U.S. Patent Publication 2007/0233273; and Hunter, Medical implants and Anti-Scarring Agents, U.S. Patent Publication 2006/0147492; Van Epps, Soft Filled Prosthesis Shell with Discrete Fixation Surfaces, International Patent Publication WO/2010/019761; Schuessler, Self Sealing Shell for Inflatable Prosthesis, International Patent Publication WO/2010/022130; Yacoub, Prosthesis Implant Shell, International Application No. PCT/US09/61045, each of which is hereby incorporated by reference in its entirety.

A biocompatible implantable device disclosed herein can be implanted into the soft tissue of an animal during the normal operation of the device. Such implantable devices may be completely implanted into the soft tissue of an animal body (i.e., the entire device is implanted within the body), or the device may be partially implanted into an animal body (i.e., only part of the device is implanted within an animal body, the remainder of the device being located outside of the animal body). A biocompatible implantable device disclosed herein can also be affixed to soft tissue of an animal during the normal operation of the medical device. Such devices are typically affixed to the skin of an animal body.

The present specification discloses, in part, a porous material that covers a surface of the biocompatible implantable device. Any of the porous materials disclosed herein can be used as the porous material covering a surface of a biocompatible implantable device. In general, the surface of a biocompatible implantable device is one exposed to the surrounding tissue of an animal in a manner that promotes tissue growth, and/or reduces or prevents formation of fibrous capsules that can result in capsular contracture or scarring.

Thus, in an embodiment, a porous material covers the entire surface of a biocompatible implantable device. In another embodiment, a porous material covers a portion of a surface of a biocompatible implantable device. In aspects of this embodiment, a porous material covers to a front surface of a biocompatible implantable device or a back surface of a biocompatible implantable device. In other aspects, a porous material covers only to, e.g., about 20%, about 30%, about 40%, about 50%, about 60%, about 70%, about 80% or about 90% of the entire surface of a biocompatible implantable device, a front surface of a biocompatible implantable device, or a back surface of a biocompatible implantable device. In yet other aspects, a porous material is applied only to, e.g., at least 20%, at least 30%, at least 40%, at least 50%, at least 60%, at least 70%, at least 80% or at least 90% of the entire surface of a biocompatible implantable device, a front surface of a biocompatible implantable device, or a back surface of a biocompatible implantable device. In still other aspects, a porous material is applied only to, e.g., at most 20%, at most 30%, at most 40%, at most 50%, at most 60%, at most 70%, at most 80% or at most 90% of the entire surface of a biocompatible implantable device, a front surface of a biocompatible implantable device, or a back surface of a biocompatible implantable device. In further aspects, a porous material is applied only to, e.g., about 20% to about 100%, about 30% to about 100%, about 40% to about 100%, about 50% to about 100%, about 60% to about 100%, about 70% to about 100%, about 80% to about 100%, or about 90% to about 100% of the entire surface of a biocompatible implantable device, a front surface of a biocompatible implantable device, or a back surface of a biocompatible implantable device.

The layer of porous material covering a biocompatible implantable device can be of any thickness with the proviso that the material thickness allows tissue growth within the array of interconnected of pores of a matrix in a manner sufficient to reduce or prevent formation of fibrous capsules that can result in capsular contracture or scarring.

Thus, in an embodiment, a layer of porous material covering a biocompatible implantable device is of a thickness that allows tissue growth within the array of interconnected of pores of a matrix in a manner sufficient to reduce or prevent formation of fibrous capsules that can result in capsular contracture or scarring. In aspects of this embodiment, a layer porous material covering a biocompatible implantable device comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a layer porous material covering a biocompatible implantable device comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a layer porous material covering a biocompatible implantable device comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a layer porous material covering a biocompatible implantable device comprises a thickness of, e.g., about 100 µm to about 500 µm, about 100 µm to about 1 mm, about 100 µm to about 5 mm, about 500 µm to about 1 mm, about 500 µm to about 2 mm, about 500 µm to about 3 mm, about 500 µm to about 4 mm, about 500 µm to about 5 mm, about 1 mm to about 2 mm, about 1 mm to about 3 mm, about 1 mm to about 4 mm, about 1 mm to about 5 mm, or about 1.5 mm to about 3.5 mm.

The present specification discloses in part, a method for making biocompatible implantable device comprising a porous material. In an aspect, a method for making biocompatible implantable device comprises the step of attaching a porous material to the surface of a biocompatible implantable device. In another aspect, a method for making biocompatible implantable device comprises the steps of a) preparing a surface of a biocompatible implantable device to receive porous material, b) attaching a porous material to the prepared surface of the device. Any of the porous materials disclosed herein can be used as the porous material attached to a surface of a biocompatible implantable device.

In yet another aspect, a method for making biocompatible implantable device comprising the step of: a) coating a mandrel with a matrix material base; b) curing the matrix material base to form a base layer; c) coating the cured base layer with a matrix material base; d) coating the matrix material base with porogens to form a matrix material-coated porogen mixture; e) treating the matrix material-coated porogen mixture to form a porogen scaffold comprising fused porogens and cure the matrix material; and f) removing the porogen scaffold, wherein porogen scaffold removal results in a porous material, the porous material comprising a matrix defining an array of interconnected pores. In this method steps (c) and (d) can be repeated multiple times until the desired thickness of the material layer is achieved.

The present specification discloses, in part, preparing a surface of a biocompatible implantable device to receive porous material. Preparing a surface of a biocompatible implantable device to receive porous material can be accomplished by any technique that does not destroy the desired properties of the porous material or the biocompatible implantable device. As a non-limiting example, a surface of a biocompatible implantable device can be prepared by applying a bonding substance. Non-limiting examples of bonding substances include silicone adhesives, such as, e.g., RTV silicone and HTV silicone. The bonding substance is applied to the surface of a biocompatible implantable device, the porous material, or both, using any method known in the art, such as, e.g., cast coating, spray coating, dip coating, curtain coating, knife coating, brush coating, vapor deposition coating, and the like.

The present specification discloses, in part, attaching a porous material to a surface of a biocompatible implantable device. The porous material can be attached to the entire surface of the device, or only to portions of the surface of the device. As a non-limiting example, porous material is attached only to the front surface of the device or only the back surface of the device. Attachment of a porous material to a surface of a biocompatible implantable device can be accomplished by any technique that does not destroy the desired properties of the porous material or the biocompatible implantable device.

For example, attachment can occur by adhering an already formed porous material onto a surface of a biocompatible implantable device using methods known in the art, such as, e.g., gluing, bonding, melting. For instance, a dispersion of silicone is applied as an adhesive onto a surface of a biocompatible implantable device, a porous material sheet, or both, and then the two materials are placed together in a manner that allows the adhesive to attached the porous material to the surface of the device in such a way that there are no wrinkles on the surface of the device. The silicone adhesive is allowed to cure and then the excess material is cut off creating a uniform seam around the device. This process results in a biocompatible implantable device comprising a porous material disclosed herein. Examples 2 and 4 illustrate method of this type of attachment.

Alternatively, attachment can occur by forming the porous material directly onto a surface of a biocompatible implantable device using methods known in the art, such as, e.g., cast coating, spray coating, dip coating, curtain coating, knife coating, brush coating, vapor deposition coating, and the like. For instance, a matrix material base is applied to a mandrel and cured to form a base layer of cured matrix material. The base layer is then initially coated with a matrix material base and then subsequently with porogens to create a matrix material-coated porogen mixture. This mixture is then treated as disclosed herein to form a porogen scaffold and cure the matrix material. The porogen scaffold is then removed, leaving a layer of porous material on the surface of the device. The thickness of the porous material layer can be increased by repeated coatings of additional matrix material base and porogens. Examples 5-8 illustrate method of this type of attachment.

Regardless of the method of attachment, the porous material can be applied to the entire surface of a biocompatible implantable device, or only to portions of the surface of a biocompatible implantable device. As a non-limiting example, porous material is applied only to the front surface of a biocompatible implantable device or only the back surface of a biocompatible implantable device.

Thus, in an embodiment, a porous material is attached to a surface of a biocompatible implantable device by bonding a porous material to a surface of a biocompatible implantable device. In aspects of this embodiment, a porous material is attached to a surface of a biocompatible implantable device by gluing, bonding, or melting the porous material to a surface of a biocompatible implantable device.

In another embodiment, a porous material is attached to a surface of a biocompatible implantable device by forming the porous material onto a surface of a biocompatible implantable device. In aspects of this embodiment, a porous material is attached to a surface of a biocompatible implantable device by cast coating, spray coating, dip coating, curtain coating, knife coating, brush coating, or vapor deposition coating.

In another aspect of this embodiment, forming a porous material on a surface of a biocompatible implantable device comprises coating a cured matrix material base layer with a matrix material base and then coating the uncured matrix material base with porogens to form a matrix material-coated porogen mixture. In other aspects of this embodiment, coating a cured matrix material base layer with an uncured matrix material base and then coating the uncured matrix material base with porogens to form a matrix material-coated porogen mixture can be repeated, e.g., at least once, at least twice, at least three times, at least four times, at least five times, at least six times, at least seven times, at least eight times, at least nine times, or at least ten times, before the mixture is treated.

In another embodiment, a porous material is applied to the entire surface of a biocompatible implantable device. In another embodiment, a porous material is applied to a portion of a surface of a biocompatible implantable device. In aspects of this embodiment, a porous material is applied to a front surface of a biocompatible implantable device or a back surface of a biocompatible implantable device. In other aspects, a porous material is applied only to, e.g., about 20%, about 30%, about 40%, about 50%, about 60%, about 70% about 80% or about 90% of the entire surface of a biocompatible implantable device, a front surface of a biocompatible implantable device, or a back surface of a biocompatible implantable device. In yet other aspects, a porous material is applied only to, e.g., at least 20%, at least 30%, at least 40%, at least 50%, at least 60%, at least 70% at least 80% or at least 90% of the entire surface of a biocompatible implantable device, a front surface of a biocompatible implantable device, or a back surface of a biocompatible implantable device. In still other aspects, a porous material is applied only to, e.g., at most 20%, at most 30%, at most 40%, at most 50%, at most 60%, at most 70% at most 80% or at most 90% of the entire surface of a biocompatible implantable device, a front surface of a biocompatible implantable device, or a back surface of a biocompatible implantable device. In further aspects, a porous material is applied only to, e.g., about 20% to about 100%, about 30% to about 100%, about 40% to about 100%, about 50% to about 100%, about 60% to about 100%, about 70% to about 100%, about 80% to about 100%, or about 90% to about 100% of the entire surface of a biocompatible implantable device, a front surface of a biocompatible implantable device, or a back surface of a biocompatible implantable device.

The layer of porous material applied to a biocompatible implantable device can be of any thickness with the proviso that the material thickness allows tissue growth within the array of interconnected of pores of a matrix in a manner sufficient to reduce or prevent formation of fibrous capsules that can result in capsular contracture or scarring.

Thus, in an embodiment, a layer of porous material applied to a biocompatible implantable device is of a thickness that allows tissue growth within the array of interconnected of pores of a matrix in a manner sufficient to reduce or prevent formation of fibrous capsules that can result in capsular contracture or scarring. In aspects of this embodiment, a layer porous material applied to a biocompatible implantable device comprises a thickness of, e.g., about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, or about 10 mm. In other aspects of this embodiment, a layer porous material applied to a biocompatible implantable device comprises a thickness of, e.g., at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In yet other aspects of this embodiment, a layer porous material applied to a biocompatible implantable device comprises a thickness of, e.g., at most 100 µm, at most 200 µm, at most 300 µm, at most 400 µm, at most 500 µm, at most 600 µm, at most 700 µm, at most 800 µm, at most 900 µm, at most 1 mm, at most 2 mm, at most 3 mm, at most 4 mm, at most 5 mm, at most 6 mm, at most 7 mm, at most 8 mm, at most 9 mm, or at most 10 mm. In still other aspects of this embodiment, a layer porous material applied to a biocompatible implantable device comprises a thickness of, e.g., about 100 µm to about 500 µm, about 100 µm to about 1 mm, about 100 µm to about 5 mm, about 500 µm to about 1 mm, about 500 µm to about 2 mm, about 500 µm to about 3 mm, about 500 μm to about 4 mm, about 500 μm to about 5 mm, about 1 mm to about 2 mm, about 1 mm to about 3 mm, about 1 mm to about 4 mm, about 1 mm to about 5 mm, or about 1.5 mm to about 3.5 mm.

EXAMPLES

The following examples illustrate representative embodiments now contemplated, but should not be construed to limit the disclosed porous materials, methods of forming such porous materials, biocompatible implantable devices comprising such porous materials, and methods of making such biocompatible implantable devices.

Example 1

A Method of Making a Porous Material Sheet

This example illustrates how to make a sheet of porous material comprising a silicone-based elastomer as disclosed herein.

To coat porogens with an elastomer base, an appropriate amount of PLGA (50/50) porogens (500 μm diameter) is mixed with an appropriate amount of 35% (w/w) silicone in xylene (MED 6400; NuSil Technology LLC, Carpinteria, Calif.). The mixture is filtered through a 43 μm sieve to remove the excess silicone and is poured into about 20 cm×20 cm square mold coated with a non-stick surface.

To treat an elastomer coated porogen mixture to allow fusing of the porogens to form a porogen scaffold and curing of the non-degradable biocompatible elastomer, the PLGA/silicone mixture is placed into an oven and is heated at a temperature of 75° C. for 45 min, and then 126° C. for 75 minutes. After curing, the sheet of cured elastomer coated porogen scaffold is removed.

To remove a porogen scaffold from the cured elastomer, the cured elastomer/porogen scaffold is immersed in methylene chloride. After 30 minutes, the methylene chloride is removed and fresh methylene chloride is added. After 30 minutes, the methylene chloride is removed and the resulting 20 cm×20 cm×1.5 mm sheet of porous material is air dried at ambient temperature. This process results in a porous material sheet as disclosed herein.

A sample from the sheet of porous material can be characterized by microCT analysis and/or scanning electron microscopy (SEM).

Porous materials of a similar characteristic are also produced using PCL porogens instead of PLGA porogens. Similarly, porogen diameters from about 50 μm to about 3000 μm can be used.

Example 2

A Method of Making a Biocompatible Implantable Device Comprising a Porous Material This example illustrates how to make a biocompatible implantable device comprising a porous material as disclosed herein.

Sheets of porous material comprising a matrix defining an interconnected array of pores is obtained as described in Example 1.

To attach a porous material to a biocompatible implantable device, a first porous material sheet is coated with a thin layer of silicone and then placed in the bottom cavity of a mold, adhesive side up. A biocompatible implantable device is then placed on top of the material surface coated with the adhesive. A second porous material sheet is then coated with a thin layer of silicone and applied to the uncovered surface of the biocompatible implantable device. The top piece of the mold cavity is then fixed in place pressing the two material sheets together creating a uniform interface. The silicone adhesive is allowed to cure by placing the covered device into an oven and heated at a temperature of 126° C. for 75 minutes. After curing, excess material is trimmed off creating a uniform seam around the biocompatible implantable device. This process results in a biocompatible implantable device comprising a porous material as disclosed herein.

Alternatively, the porous material can be laminated onto a biocompatible implantable device while the device is still on a mandrel. In this process, a first porous material sheet is coated with a thin layer of silicone and then draped over the device on the mandrel in such a way that there are no wrinkles on the surface. After curing the silicone adhesive, as described above, another coating of silicone is applied to the uncovered surface of the biocompatible implantable device and a second porous material is stretched up to cover the back of the device. After curing the silicone adhesive, as described above, the biocompatible implantable device is then taken off the mandrel and the excess porous material is trimmed to create a uniform seam around the device. This process results in a biocompatible implantable device comprising a porous material as disclosed herein.

Example 3

A Method of Making a Porous Material Shell

This example illustrates how to make a shell including a porous material comprising a silicone-based elastomer as disclosed herein.

To coat porogens with a non-degradable biocompatible elastomer, an appropriate amount of PLGA (50/50) porogens (500 μm diameter) is mixed with an appropriate amount of 35% (w/w) silicone in xylene (MED 6400; NuSil Technology LLC, Carpinteria, Calif.). The mixture is filtered through a 43 μm sieve to remove the excess silicone.

The filtered elastomer coated porogen mixture is poured into a mold in the shape of a breast implant shell and the mold is mechanically agitated to pack firmly the mixture. The thickness of the shell is controlled based upon the design of the shell mold.

To treat a matrix material-coated porogen mixture to allow fusing of the porogens to form a porogen scaffold and curing of the non-degradable biocompatible elastomer, the PLGA/silicone mixture is placed into an oven and is heated at a temperature of 75° C. for 45 min, and then 126° C. for 75 minutes. After curing, the shell mold is dismantled and the cured elastomer coated porogen scaffold is removed.

To remove a porogen scaffold from the cured elastomer, the cured elastomer/porogen scaffold is immersed in methylene chloride. After 30 minutes, the methylene chloride is removed and fresh methylene chloride is added. After 30 minutes, the methylene chloride is removed and the resulting 30 cm×30 cm×1.5 mm sheet of porous material is air dried at an ambient temperature of about 18° C. to about 22° C. This process results in a porous material shell as disclosed herein.

A sample from the sheet of porous material can be characterized by microCT analysis and/or scanning electron microscopy (SEM).

Porous materials of a similar characteristic are also produced using PCL porogens instead of PLGA porogens. Similarly, porogen diameters from about 50 μm to about 3000 μm can be used.

Example 4

A Method of Making a Medical Device Including a Porous Material Surface

This example illustrates how to make a medical device including a porous material surface disclosed herein.

A porous material shell comprising a matrix defining an interconnected array of pores is obtained as described in Example 3.

To attach the porous material shell to a medical device, for example, an implantable article such as a pacemaker or artificial valve, the surface of the device is coated with a thin layer of silicone. The material shell is then placed over the adhesive coated device in a manner that ensures no wrinkles in the material form. The silicone adhesive is cure by placing the covered device into an oven and heating at a temperature of 126° C. for 75 minutes. After curing, excess material is trimmed off creating a uniform seam around the device. This process results in an implantable medical device comprising a porous material surface as disclosed herein.

Example 5

A Method of Making an Implant Comprising a Porous Material

This example illustrates how to make an implant comprising a porous material disclosed herein of about 0.5 mm to about 1.5 mm in thickness.

To prepare the surface of a device to receive a porous material, a base layer of 35% (w/w) silicone in xylene (MED4810; NuSil Technology LLC, Carpinteria, Calif.) was coated on a mandrel (LR-10), placed into an oven, and cured at a temperature of 126° C. for 75 minutes.

To coat the base layer with a mixture comprising a non-degradable biocompatible elastomer and porogens, the cured base layer was dipped first in 35% (w/w) silicone in xylene (MED4810; NuSil Technology LLC, Carpinteria, Calif.) and then air dried for about 3 minutes to allow the xylene to evaporate. After xylene evaporation, the Mandrel with the uncured silicone was dipped in PLGA porogens until the maximum amount of porogens were absorbed into the uncured silicone. The Mandrel with the uncured silicone/PGLA coating was air dried for about 60 minutes to allow the xylene to evaporate.

To treat an elastomer coated porogen mixture to allow fusing of the porogens to form a porogen scaffold and curing of the non-degradable biocompatible elastomer, the Mandrel coated with the uncured silicone/PLGA mixture was placed into an oven and cured at a temperature of 75° C. for 30 min, and then 126° C. for 75 minutes.

To remove porogen scaffold, the cured silicone/PLGA mixture was immersed in methylene chloride. After 30 minutes, the methylene chloride was removed and fresh methylene chloride was added. After 30 minutes, the methylene chloride was again removed and fresh methylene chloride was added. After 30 minutes, the methylene chloride was removed and the resulting implant comprising a porous material of about 0.5 mm to about 1.5 mm was air dried at an ambient temperature of about 18° C. to about 22° C. This process results in a biocompatible implantable device comprising a porous material as disclosed herein.

A sample from the implant was characterized by SEM. This analysis revealed that the porous material was about 1.4 mm to about 1.6 mm in thickness.

Porous materials of a similar characteristic are also produced using PCL porogens instead of PLGA porogens. Similarly, porogen diameters from about 50 µm to about 3000 µm can be used.

To increase the thickness of the porous material covering the base layer, multiple dippings were performed to produce a mandrel coated with multiple layers of an uncured silicone/porogen mixture. Dippings were repeated until the desired thickness is achieved. Examples 4-6 below describe specific examples of this multiple dipping technique.

Example 6

A Method of Making an Implant Comprising a Porous Material

This example illustrates how to make an implant comprising a porous material disclosed herein of about 1 mm to about 2.5 mm in thickness.

A mandrel comprising a base layer of elastomer was prepared as described in Example 3.

To coat the base layer with a mixture comprising a non-degradable biocompatible elastomer and porogens, the cured base layer was dipped first in 35% (w/w) silicone in xylene (MED4810; NuSil Technology LLC, Carpinteria, Calif.) and then air dried for about 3 minutes to allow the xylene to evaporate. After xylene evaporation, the mandrel with the uncured silicone was dipped in PLGA porogens until the maximum amount of porogens were absorbed into the uncured silicone. The mandrel with the uncured silicone/PGLA coating was air dried for about 60 minutes to allow the xylene to evaporate. After xylene evaporation, the mandrel coated with the uncured silicone/PLGA porogen mixture was dipped first in 35% (w/w) silicone in xylene, air dried to allow xylene evaporation (about 3 minutes), and then dipped in PLGA porogens until the maximum amount of porogens were absorbed into the uncured silicone. The mandrel with the second coating of uncured silicone/PGLA porogen mixture was air dried for about 60 minutes to allow the xylene to evaporate.

The mandrel comprising the two coats of uncured silicone/PLGA porogen mixture was treated as described in Example 3.

To remove porogen scaffold, the cured silicone/PLGA mixture was immersed in methylene chloride. After 30 minutes, the methylene chloride was removed and fresh methylene chloride was added. After 30 minutes, the methylene chloride was again removed and fresh methylene chloride was added. After 30 minutes, the methylene chloride was removed and the resulting implant comprising a porous material of about 1 mm to about 2.5 mm was air dried at an ambient temperature of about 18° C. to about 22° C. This process results in a biocompatible implantable device comprising a porous material as disclosed herein.

A sample from the implant was characterized by SEM and microCT analysis. This analysis revealed that the porous material was about 2 mm to about 2.5 mm in thickness with a porosity of about 88%.

Porous materials of a similar characteristic are also produced using PCL porogens instead of PLGA porogens. Similarly, porogen diameters from about 50 µm to about 3000 µm can be used.

Example 7

A Method of Making an Implant Comprising a Porous Material

This example illustrates how to make an implant comprising a porous material disclosed herein of about 2.5 mm to about 4.5 mm in thickness.

A mandrel comprising a base layer of elastomer was prepared as described in Example 3.

To coat the base layer with a mixture comprising a non-degradable biocompatible elastomer and porogens, the cured base layer was dipped first in 35% (w/w) silicone in xylene (MED4810; NuSil Technology LLC, Carpinteria, Calif.) and then air dried for about 3 minutes to allow the xylene to evaporate. After xylene evaporation, the mandrel with the uncured silicone was dipped in PLGA porogens until the maximum amount of porogens were absorbed into the uncured silicone. The mandrel with the uncured silicone/PGLA coating was air dried for about 60 minutes to allow the xylene to evaporate. After xylene evaporation, the mandrel coated with the uncured silicone/PLGA porogen mixture was dipped first in 35% (w/w) silicone in xylene, air dried to allow xylene evaporation (about 3 minutes), and then dipped in PLGA porogens until the maximum amount of porogens were absorbed into the uncured silicone. The mandrel with the second coating of uncured silicone/PGLA was air dried for about 60 minutes to allow the xylene to evaporate. After xylene evaporation, the mandrel coated with the two layers of the uncured silicone/PLGA porogen mixture was dipped first in 32% (w/w) silicone in xylene, air dried to allow xylene evaporation (about 3 minutes), and then dipped in PLGA porogens until the maximum amount of porogens were absorbed into the uncured silicone. The mandrel with the third coating of uncured silicone/PGLA porogen mixture was air dried for about 60 minutes to allow the xylene to evaporate.

The mandrel comprising the two coats of uncured silicone/PLGA porogens was treated as described in Example 3.

To remove porogen scaffold, the cured silicone/PLGA mixture was immersed in methylene chloride. After 30 minutes, the methylene chloride was removed and fresh methylene chloride was added. After 30 minutes, the methylene chloride was again removed and fresh methylene chloride was added. After 30 minutes, the methylene chloride was removed and the resulting implant comprising a porous material of about 2.5 mm to about 4.5 mm was air dried at an ambient temperature of about 18° C. to about 22° C. This process results in a biocompatible implantable device comprising a porous material as disclosed herein.

A sample from the implant was characterized by SEM and microCT analysis. This analysis revealed that the porous material was about 3.5 mm to about 4.5 mm in thickness.

Porous materials of a similar characteristic are also produced using PCL porogens instead of PLGA porogens. Similarly, porogen diameters from about 50 µm to about 3000 µm can be used.

Example 8

A Method of Making an Implant Comprising a Porous Material

This example illustrates how to make an implant comprising a porous material disclosed herein of about 3.5 mm to about 5.5 mm in thickness.

A mandrel comprising a base layer of elastomer was prepared as described in Example 3.

To coat the base layer with a mixture comprising a non-degradable biocompatible elastomer and porogens, the cured base layer was dipped first in 35% (w/w) silicone in xylene (MED4810; NuSil Technology LLC, Carpinteria, Calif.) and then air dried for about 3 minutes to allow the xylene to evaporate. After xylene evaporation, the Mandrel with the uncured silicone was dipped in PLGA porogens until the maximum amount of porogens were absorbed into the uncured silicone. The mandrel with the uncured silicone/PGLA coating was air dried for about 60 minutes to allow the xylene to evaporate. After xylene evaporation, the mandrel coated with the uncured silicone/PLGA porogen mixture was dipped first in 35% (w/w) silicone in xylene, air dried to allow xylene evaporation (about 3 minutes), and then dipped in PLGA porogens until the maximum amount of porogens were absorbed into the uncured silicone. The mandrel with the second coating of uncured silicone/PGLA was air dried for about 60 minutes to allow the xylene to evaporate. After xylene evaporation, the mandrel coated with the two layers of the uncured silicone/PLGA porogen mixture was dipped first in 32% (w/w) silicone in xylene, air dried to allow xylene evaporation (about 3 minutes), and then dipped in PLGA porogens until the maximum amount of porogens were absorbed into the uncured silicone. The mandrel with the third coating of uncured silicone/PG LA porogen mixture was air dried for about 60 minutes to allow the xylene to evaporate. After xylene evaporation, the mandrel coated with the three layers of the uncured silicone/PLGA porogen mixture was dipped first in 28% (w/w) silicone in xylene, air dried to allow xylene evaporation (about 3 minutes), and then dipped in PLGA porogens until the maximum amount of porogens were absorbed into the uncured silicone. The mandrel with the fourth coating of uncured silicone/PGLA porogen mixture was air dried for about 60 minutes to allow the xylene to evaporate.

The mandrel comprising the two coats of uncured silicone/PLGA porogens was treating as described in Example 3.

To remove porogen scaffold, the cured silicone/PLGA mixture was immersed in methylene chloride. After 30 minutes, the methylene chloride was removed and fresh methylene chloride was added. After 30 minutes, the methylene chloride was again removed and fresh methylene chloride was added. After 30 minutes, the methylene chloride was removed and the resulting implant comprising a porous material of about 3.5 mm to about 5.5 mm was air dried at an ambient temperature of about 18° C. to about 22° C. This process results in a biocompatible implantable device comprising a porous material as disclosed herein.

A sample from the implant was characterized by microCT analysis. This analysis revealed that the porous material was about 4.5 mm to about 5.5 mm in thickness.

Porous materials of a similar characteristic are also produced using PCL porogens instead of PLGA porogens. Similarly, porogen diameters from about 50 µm to about 3000 µm can be used.

Example 9

A Method of Making a Porous Material Comprising a Carbon-Based Elastomer

This example illustrates how to make a porous material comprising a rubber as disclosed herein.

To coat porogens with a carbon-based elastomer base, an appropriate amount of PMMA porogens (350 µm diameter) is mixed with an appropriate amount of a carbon-based elastomer base, such as, e.g., poly(isoprene), poly(butadiene), poly(isobutylene isoprene), poly(butadiene acrylonitrile), and poly(chloroprene). The mixture is filtered through a 43 µm sieve to remove the excess rubber and is poured into about 20 cm×20 cm square mold coated with a non-stick surface.

To treat a carbon-based elastomer base-coated porogen mixture to allow fusing of the porogens to form a porogen scaffold and curing of the elastomer, the rubber/PMMA mixture is placed into an oven and is heated at a temperature of 70° C. to soften the rubber, sulfur and zinc oxide are added, and then this mixture is heated to 126° C. for 75 minutes. After curing, the sheet of cured elastomer coated porogen scaffold is removed.

To remove a porogen scaffold from the cured carbon-based elastomer, the cured rubber/PMMA scaffold is immersed in acetone or chloroform. After 30 minutes, the acetone or chloroform is removed and fresh acetone or chloroform is added. After 30 minutes, the acetone or chloroform is removed and the resulting 20 cm×20 cm×1.5 mm sheet of porous material is air dried at ambient temperature. This process results in a porous material sheet as disclosed herein.

A sample from the sheet of porous material can be characterized by microCT analysis and/or scanning electron microscopy (SEM). The porous material may be further engineered for different applications.

Porous materials of a similar characteristic are also produced using polystyrene, PCL, PGLA, or sugar porogens instead of PMMA porogens. Similarly, porogen diameters from about 50 µm to about 3000 µm can be used. Likewise, the porous material may be affixed to another component in a manner similar to that described in Example 2. Similarly, the porous material may be shaped using a mold in a manner similar to that described in Example 3 and/or affixed to another component in a manner similar to that described in Example 4. Furthermore, the porous material may be part of a manufacturing process where it is integrated as a component in a manner similar to that described in Examples 5-8.

Example 10

A Method of Making a Porous Material Comprising a Poly(Vinyl)-Based Thermoplastic This example illustrates how to make a porous material comprising a thermoplastic as disclosed herein.

To coat porogens with an thermoplastic base, an appropriate amount of sugar porogens (650 µm diameter) is mixed with an appropriate amount of poly(vinyl)-based thermoplastic, such as, e.g., poly(vinyl chloride), poly(vinylidene fluoride), poly(vinyl fluoride), poly(vinyl nitrate), and poly-(4-vinylphenol). The mixture is filtered through a 43 µm sieve to remove the excess poly(vinyl)-based thermoplastic and is poured into about 20 cm×20 cm square mold coated with a non-stick surface.

To treat a thermoplastic-coated porogen mixture to allow fusing of the porogens to form a porogen scaffold and hardening of the thermoplastic, the poly(vinyl)-based thermoplastic/sugar mixture is placed into an oven and is heated at a temperature of 90° C. to soften the poly(vinyl)-based thermoplastic, and then this mixture is heated to 120° C. for 30 minutes to fuse sugar porogens. The mixture is cooled to room temperature to allow hardening of the poly(vinyl)-based thermoplastic. After hardening, the sheet of hardened poly(vinyl)-based thermoplastic-coated porogen scaffold is removed.

To remove a porogen scaffold from the cured elastomer, the hardened poly(vinyl)-based thermoplastic/sugar scaffold is immersed in warm water. After 30 minutes, the water is removed and fresh warm water is added. After 30 minutes, the water is removed and the resulting 20 cm×20 cm×1.5 mm sheet of porous material is air dried at ambient temperature. This process results in a porous material sheet as disclosed herein.

A sample from the sheet of porous material can be characterized by microCT analysis and/or scanning electron microscopy (SEM). The porous material may be further engineered for different applications.

Porous materials of a similar characteristic are also produced using polystyrene, PCL, PGLA, PMMA, or polystyrene porogens instead of sugar porogens. Similarly, porogen diameters from about 50 µm to about 3000 µm can be used. Likewise, the porous material may be affixed to another component in a manner similar to that described in Example 2. Similarly, the porous material may be shaped using a mold in a manner similar to that described in Example 3 and/or affixed to another component in a manner similar to that described in Example 4. Furthermore, the porous material may be part of a manufacturing process where it is integrated as a component in a manner similar to that described in Examples 5-8.

Example 11

A Method of Making a Porous Material Comprising Thermoplastic Elastomer

This example illustrates how to make a porous material comprising a thermoplastic elastomer as disclosed herein.

To coat porogens with an thermoplastic elastomer base, an appropriate amount of sugar porogens (250 µm diameter) is mixed with an appropriate amount of a thermoplastic elastomer, such as, e.g., poly(styrene-co-butadiene-polystyrene) (SBS). The mixture is filtered through a 43 µm sieve to remove the excess SBS and is poured into about 20 cm×20 cm square mold coated with a non-stick surface.

To treat a thermoplastic elastomer-coated porogen mixture to allow fusing of the porogens to form a porogen scaffold and curing of the thermoplastic elastomer, the SBS/sugar mixture is placed into an oven and is heated at a temperature of 90° C. to soften the SBS, and then this mixture is heated to 120° C. for 30 minutes to fuse sugar porogens. After curing, the sheet of hardened SBS-coated porogen scaffold is removed.

To remove a porogen scaffold from the cured elastomer, the hardened poly(vinyl)-based thermoplastic/sugar scaffold is immersed in warm water. After 30 minutes, the water is removed and fresh warm water is added. After 30 minutes, the water is removed and the resulting 20 cm×20 cm×1.5 mm sheet of porous material is air dried at ambient temperature. This process results in a porous material sheet as disclosed herein.

A sample from the sheet of porous material can be characterized by microCT analysis and/or scanning electron microscopy (SEM). The porous material may be further engineered for different applications.

Porous materials of a similar characteristic are also produced using polystyrene, PCL, PGLA, PMMA, or polystyrene porogens instead of sugar porogens. Similarly, porogen diameters from about 50 µm to about 3000 µm can be used. Likewise, the porous material may be affixed to another component in a manner similar to that described in Example 2. Similarly, the porous material may be shaped using a mold in a manner similar to that described in Example 3 and/or affixed to another component in a manner similar to that described in Example 4. Furthermore, the porous material may be part of a manufacturing process where it is integrated as a component in a manner similar to that described in Examples 5-8.

Example 12

A Method of Making a Porous Material Comprising a Thermoset Elastomer

This example illustrates how to make a porous material comprising a thermoset elastomer as disclosed herein.

To coat porogens with an thermoset elastomer base, an appropriate amount of PMMA porogens (1,000 µm diameter) is mixed with an appropriate amount of a poly(urethane). The mixture is filtered through a 43 µm sieve to remove the excess poly(urethane) and is poured into about 20 cm×20 cm square mold coated with a non-stick surface.

To treat a thermoset elastomer-coated porogen mixture to allow fusing of the porogens to form a porogen scaffold and curing of the thermoset elastomer, the poly(urethane)/PMMA mixture is placed into an oven and is heated at a temperature of 126° C. for 75 minutes. After curing, the sheet of cured elastomer coated porogen scaffold is removed.

To remove a porogen scaffold from the cured elastomer, the cured poly(urethane)/PMMA scaffold is immersed in acetone or chloroform. After 30 minutes, the acetone or chloroform is removed and fresh acetone or chloroform is added. After 30 minutes, the acetone or chloroform is removed and the resulting 20 cm×20 cm×1.5 mm sheet of porous material is air dried at ambient temperature. This process results in a porous material sheet as disclosed herein.

A sample from the sheet of porous material can be characterized by microCT analysis and/or scanning electron microscopy (SEM). The porous material may be further engineered for different applications.

Porous materials of a similar characteristic are also produced using polystyrene, PCL, PGLA, sugar, or polystyrene porogens instead of PMMA porogens. Similarly, porogen diameters from about 50 µm to about 3000 µm can be used. Likewise, the porous material may be affixed to another component in a manner similar to that described in Example 2. Similarly, the porous material may be shaped using a mold in a manner similar to that described in Example 3 and/or affixed to another component in a manner similar to that described in Example 4. Furthermore, the porous material may be part of a manufacturing process where it is integrated as a component in a manner similar to that described in Examples 5-8.

It can be appreciated that porous materials are provided by the present invention can have numerous industrial, household and medical uses. For example, porous materials in the biomedical field are provided which can be components of devices and articles useful for tissue engineering/regeneration, wound dressings, drug release matrices, membranes for separations and filtration, sterile filters, artificial kidneys, absorbents, hemostatic devices, and the like. In various industrial and household applications, porous materials are provided which can make up insulating materials, packaging materials, impact absorbers, liquid or gas absorbents, and wound dressings. The material provided also can be used as components of personal hygiene products, such as but not limited to, cleaning and cleansing pads, wipes and swabs, deodorant, disposable towels, dry shampoo, facial tissues, handkerchiefs, hygiene wipes, paper towels, shaving brushes, tampons, towels, underarm liners, washing mitts, and wet wipes, membranes, filters and so forth. Many other uses are contemplated for the present materials and are considered to be within the scope of the invention.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for forming a porous material, the method comprising the steps of:
    a) coating porogens with a matrix material base to form a matrix material-coated porogen mixture;
    b) filtering the matrix material-coated porogen mixture through a sieve to remove excess matrix material;
    c) pouring the filtered mixture into a mold;
    d) treating the filtered mixture to form a scaffold comprising fused porogens and cured matrix material, wherein the scaffold comprises a three-dimensional structure in the form of the mold; and
    e) removing the fused porogens from the scaffold, wherein fused porogen removal results in a porous material comprising the cured matrix material defining an array of interconnected pores.

2. The method of claim 1 wherein in the scaffold comprises a three-dimensional structure wherein the diameter of substantially all the connections between each fused porogen in between about 15% to about 80% of the mean porogen diameter.

3. The method of claim 1 wherein the cured matrix material exhibits an elastic elongation of at least 80%.

4. The method of claim 1 wherein the matrix material is a silicone elastomer.

* * * * *

UNITED STATES PATENT AND TRADEMARK OFFICE
CERTIFICATE OF CORRECTION

PATENT NO.        : 8,889,751 B2
APPLICATION NO.   : 13/247835
DATED             : November 18, 2014
INVENTOR(S)       : Futian Liu et al.

It is certified that error appears in the above-identified patent and that said Letters Patent is hereby corrected as shown below:

In the Specification

In column 1, line 8, delete "polymeric;" and insert -- polymeric --, therefor.

In column 1, line 22, delete "synthetic;" and insert -- synthetic --, therefor.

In column 3, line 32, delete "herein," and insert -- herein. --, therefor.

In column 3, line 48, delete "racemic" and insert -- racemo --, therefor.

In column 3, line 54, delete "polyethers, polyethers," and insert -- polyethers, --, therefor.

In column 5, line 14, delete "(TO" and insert -- $(T_g)$ --, therefor.

In column 5, line 37, delete "elastomer," and insert -- elastomer. --, therefor.

In column 5, line 41, delete "(BUR)," and insert -- (BIIR), --, therefor.

In column 5, line 42, delete "(CHR)," and insert -- (CIIR), --, therefor.

In column 5, line 48, delete "nitrile," and insert -- nitrile --, therefor.

In column 5, line 51, delete "(Si)," and insert -- (SI), --, therefor.

In column 5, line 53, delete "(RB)," and insert -- (PIB), --, therefor.

In column 5, line 64, delete "scone-based" and insert -- silicone-based --, therefor.

In column 5, line 66, delete "scone," and insert -- silicone, --, therefor.

In column 5, line 66-67, delete "scone-based" and insert -- silicone-based --, therefor.

In column 7, line 63, delete "$(L_0)$," and insert -- $(L_O)$, --, therefor.

In column 14, line 49, delete "$W \cdot K^{-1} \, m^{-2}$." and insert -- $W \cdot K^{-1} m^{-2}$. --, therefor.

In column 14, line 57, delete "$Wm^{-1}K^{-1}$" and insert -- $Wm^{-1}K^{-1}$, --, therefor.

In column 23, line 39, delete "um" and insert -- μm --, therefor.

In column 24, line 10, delete "flack" and insert -- flak --, therefor.

In column 26, line 12, delete "arylic" and insert -- acrylic --, therefor.

In column 26, line 20, delete "((like" and insert -- (like --, therefor.

Signed and Sealed this
Fifth Day of May, 2015

Michelle K. Lee
*Director of the United States Patent and Trademark Office*

CERTIFICATE OF CORRECTION (continued)
U.S. Pat. No. 8,889,751 B2

In column 26, line 23, after "poly(lactide)" insert -- (like --.

In column 26, line 45, delete "Polyscience" and insert -- Polysciences --, therefor.

In column 28, line 19, delete "sublimination," and insert -- sublimation, --, therefor.

In column 30, line 67, delete "different, different," and insert -- different. --, therefor.

In column 38, line 24, delete "in" and insert -- In --, therefor.

In column 38, line 46, delete "scaffold, in" and insert -- scaffold. In --, therefor.

In column 44, line 6, delete "70%" and insert -- 70%, --, therefor.

In column 44, line 12, delete "70%" and insert -- 70%, --, therefor.

In column 44, line 18, delete "70%" and insert -- 70%, --, therefor.

In column 47, line 46, delete "PGLA" and insert -- PLGA --, therefor.

In column 48, line 29, delete "PGLA" and insert -- PLGA --, therefor.

In column 48, line 36, delete "PGLA" and insert -- PLGA --, therefor.

In column 49, line 12, delete "PGLA" and insert -- PLGA --, therefor.

In column 49, line 19, delete "PGLA" and insert -- PLGA --, therefor.

In column 49, line 27, delete "PGLA" and insert -- PLGA --, therefor.

In column 50, line 3, delete "PGLA" and insert -- PLGA --, therefor.

In column 50, line 10, delete "PGLA" and insert -- PLGA --, therefor.

In column 50, line 18, delete "PG LA" and insert -- PLGA --, therefor.

In column 50, line 26, delete "PGLA" and insert -- PLGA --, therefor.

In column 51, line 20, delete "PGLA," and insert -- PLGA, --, therefor.

In column 52, line 6, delete "PGLA," and insert -- PLGA, --, therefor.

In column 52, line 49, delete "PGLA," and insert -- PLGA, --, therefor.

In column 53, line 26, delete "PGLA," and insert -- PLGA, --, therefor.